(12) United States Patent
Suwalski et al.

(10) Patent No.: US 8,635,081 B2
(45) Date of Patent: Jan. 21, 2014

(54) INTEGRATED PHARMACY ERROR TRACKING AND REPORTING SYSTEM AND METHOD

(75) Inventors: Michael William Suwalski, South Elgin, IL (US); Charles Goodall, Hawthorn Woods, IL (US); Sam Libo, Deerfield, IL (US); Christopher Shogun Moy, Wheeling, IL (US); Amanda Eileen White, Schaumburg, IL (US)

(73) Assignee: Walgreen Co., Deerfield, IL (US)

( * ) Notice: Subject to any disclaimer, the term of this patent is extended or adjusted under 35 U.S.C. 154(b) by 2730 days.

(21) Appl. No.: 11/264,363

(22) Filed: Nov. 1, 2005

(65) Prior Publication Data

US 2007/0100662 A1 May 3, 2007

(51) Int. Cl.
*G06Q 10/00* (2012.01)
*G06Q 50/00* (2012.01)

(52) U.S. Cl.
USPC .................................................. 705/2; 705/3

(58) Field of Classification Search
None
See application file for complete search history.

(56) References Cited

U.S. PATENT DOCUMENTS

| | | | |
|---|---|---|---|
| 5,628,530 A | 5/1997 | Thornton | |
| 5,832,449 A | 11/1998 | Cunningham | |
| 6,859,780 B1 | 2/2005 | Cunningham | |
| 7,020,697 B1 * | 3/2006 | Goodman et al. | 709/223 |
| 2003/0074225 A1 | 4/2003 | Borsand et al. | |
| 2003/0144884 A1 | 7/2003 | Mayaud | |
| 2004/0088187 A1 | 5/2004 | Chudy et al. | |
| 2004/0148195 A1 | 7/2004 | Kalies | |
| 2005/0033610 A1 | 2/2005 | Cunningham | |
| 2005/0060197 A1 | 3/2005 | Mayaud | |
| 2005/0071193 A1 | 3/2005 | Kalies | |
| 2005/0080651 A1 | 4/2005 | Morrison et al. | |
| 2005/0090425 A1 | 4/2005 | Reardan et al. | |
| 2005/0154627 A1 | 7/2005 | Zuzek et al. | |

OTHER PUBLICATIONS

Mekhjian et al., "Development of a Web-based Event Reporting System in an Academic Environment" Journal of the American Medical Informatics Association; Jan./Feb. 2004; 11, 1; pp. 11-18.*

* cited by examiner

*Primary Examiner* — Eliza Lam
(74) *Attorney, Agent, or Firm* — James P. Muraff; Neal, Gerber & Eisenberg LLP

(57) ABSTRACT

The disclosure presents a system and method for efficiently capturing, tracking, analyzing, and providing continuous quality improvement in an integrated manner in relation to errors which occur in the distribution of medication to patients through a multi-store pharmacy operation. The system and method include receiving error event data for a pharmacy error event through a first input device at a pharmacy through an input interface, transmitting the error event data to a pharmacy error event database associated with a pharmacy error event computer and storing the error event data in the pharmacy error event database. The system and method may also determine whether the first error event information requires escalation, and transmit an error event escalation message through a communication device to supervisory personnel, as well as tabulate the error event data with the pharmacy error event computer based on a criteria for communicating insight information to supervisory personnel through a communication device. The system and method provide further structural, functional and operational features for implementing these and other features in a multi-store and multi-district pharmacy operation.

16 Claims, 28 Drawing Sheets

*FIG. 6*

Event Information
- Event Type: Please Select ▼  — 2215
- Was the medication used? ● Yes ○ No — 2220
- How many doses were used? ☐ Unknown — 2225
- Patient's Alleged Health Condition: Unknown ▼ — 2230
- Patient's Alleged Attitude: Unknown ▼ — 2235

Tabs: Enter Script # | EZ-Form | Event Recap | Event Details | Follow-Up Actions — 2210

Buttons: Back | Save As Draft | Continue | Cancel

2200

Follow Up Actions

Did patient return incorrect medication? ● Yes ○ No ○ Unknown — 2510
Did patient receive correct medication? ● Yes ○ No ○ Unknown — 2520
Was the doctor contacted? ● Yes ○ No ○ Unknown — 2530
MD Comments: [◄ ►] — 2540

Did patient receive a refund? ● Yes ○ No ○ Unknown — 2550
Was insurance notified (per Supervisor)? ● Yes ○ No ○ Unknown  Claim # [  ] — 2562, 2560
OutWindow staff initials: [  ] ● Unknown — 2570

[Back]  [Save As Draft]  [Submit] — 2580  [Cancel]

| | LAB | | Employee Q | | Peer Review | Reports | |
|---|---|---|---|---|---|---|---|
| | | | | | | Logout | |
| | | | | | | | Page 1 of 1 |
| Confidential: Peer Review Document - DO NOT PRINT OR DUPLICATE | | | | | | | |
| Store No. | Event No. | Date | Patient Name | Event Type | Patient Condition | Patient Attitude | Reviewed |
| 8293 | 120383-1 | 09/22/2004 | KING LUCY | Incorrect Patient | No Adverse Rx Reported | Concerned | No |
| 8293 | 120383-2 | 09/22/2004 | KING LUCY | Incorrect Drug | Adverse Rx Reported | Concerned | No |
| 8293 | 120383-3 | 09/22/2004 | KING LUCY | Incorrect Strength | No Adverse Rx Reported | Concerned | No |
| 8293 | 120383-4 | 09/22/2004 | KING LUCY | Incorrect Strength | Unknown | Not Concerned | No |
| 8293 | 120384-1 | 09/22/2004 | KING LUCY | Incorrect Strength | No Adverse Rx Reported | Very Concerned | No |
| 8294 | 120056-1 | 09/22/2004 | TEST BILL | Incorrect Drug | No Adverse Rx Reported | Not Concerned | No |

| | District Q | Store Q | Employee Q | New Event | Peer Review | Reports | |
|---|---|---|---|---|---|---|---|
| | | | | | | Logout | |

District Number: 54 ▼

Confidential: Peer Review Document - DO NOT PRINT OR DUPLICATE

| Event# | Store# | Date Filed | Patient Name | Event Type | Patient Condition | Doses Taken | Patient Attitude | Status |
|---|---|---|---|---|---|---|---|---|
| 60009-4 | 8294 | 09/30/2004 | HOUSEHOLD, HEAD | Incorrect Strength | No Adverse Rx Reported | Unk | Not Concerned | Store Draft |
| 120298-1 | 8294 | 09/27/2004 | KING, KATHY | Incorrect Patient | Unknown | Unk | Unknown | Store Draft |
| 120045-1 | 8294 | 09/24/2004 | TESTPATIENT, MARY | Adverse Drug Reaction | Deceased | Yes | Extremely Upset | Store Draft |
| 120041-2 | 8294 | 09/21/2004 | KING, LUCY | Incorrect Strength | Unknown | Unk | Unknown | Store Draft |
| 180467-1 | 8293 | 09/24/2004 | GHOST, CASPER | Incorrect Package to Patient | Adverse Rx Reported | 1 | Concerned | Submitted to RxS |
| 180453-1 | 8293 | 09/24/2004 | GHOST, CASPER | Incorrect Drug | Adverse Rx Reported | No | Concerned | Submitted to RxS |
| 120411-1 | 8293 | 09/24/2004 | KING, LUCY | Adverse Drug Reaction | Deceased | Yes | Extremely Upset | Submitted to RxS |
| 120050-2 | 8294 | 09/23/2004 | HARDY, HELEN | Incorrect Directions | Adverse Rx Reported | Yes | Extremely Upset | Submitted to RxS |
| 120397-1 | 8293 | 09/23/2004 | KING, LUCY | Other | Required Md Office Visit | Unk | Very Concerned | Submitted to RxS |
| 120397-2 | 8293 | 09/23/2004 | KING, LUCY | Other | No Adverse Rx Reported | Unk | Not Concerned | Submitted to RxS |
| 120397-3 | 8293 | 09/23/2004 | KING, LUCY | Other | Adverse Rx Reported | Unk | Concerned | Submitted to RxS |
| 120393-2 | 8293 | 09/23/2004 | KING, LUCY | Adverse Drug Reaction | No Adverse Rx Reported | Unk | Not Concerned | Submitted to RxS |
| 120211-1 | 8294 | 09/22/2004 | CLOONEY, GEORGE | Incorrect Directions | Hospitalized | Yes | Unknown | Submitted to RxS |
| 120383-1 | 8293 | 09/22/2004 | KING, LUCY | Incorrect Patient | No Adverse Rx Reported | Unk | Concerned | Submitted to RxS |
| 120383-2 | 8293 | 09/22/2004 | KING, LUCY | Incorrect Drug | Adverse Rx Reported | Unk | Concerned | Submitted to RxS |

Next | Last   Page 1 of 5

Filter: All ▼   Filter Data   All ▼   All ▼   From: ▦   To: ▦   Clear Dates

| District Q | Store Q | Employee Q | New Event | Peer Review | Reports |

Logout

Confidential: Peer Review Document - DO NOT PRINT OR DUPLICATE

STARS External Event Information

Event #: 180467
Store #: 8293
Fill Date: 09/24/2004

Event Type: Incorrect Package to Patient
Medication Taken: Yes
Doses Taken: 1
Alleged Patient Health Condition: Adverse Rx Reported
Alleged Patient Attitude: Concerned

Patient Information:

Name: GHOST, CASPER    Address: 2666 SPOOKY CEMETERY DRIVE    Gender: M
DOB: 01/01/1800                   TRANSILVANIA, NY 60015        Phone: (847)914-5360

Comments:

Settlement Made: ● Yes ○ No

Page Up    Page Down    Cancel

Submit to QA — 3224
Save as Draft — 3226
Reject — 3222
Extra Deadline — 3228

| District Q | Store Q | Employee Q | New Event | Peer Review | Reports |

Logout

STARS External Event Information

Confidential: Peer Review Document - DO NOT PRINT OR DUPLICATE

Event #: 180467
Store #: 8293
Fill Date: 09/24/2004

Event Type: Incorrect Package to Patient
Medication Taken: Yes
Doses Taken: 1
Alleged Patient Health Condition: Adverse Rx Reported
Alleged Patient Attitude: Concerned

Patient Information:

| Name: | GHOST, CASPER | Address: | 2666 SPOOKY CEMETERY DRIVE | Gender: | M |
| DOB: | 01/01/1800 | | TRANSILVANIA, NY 60015 | Phone | (847)914-5360 |

Prescription Information

| | | | |
|---|---|---|---|
| RX #: | 180467-8293 Last Refill: 09/24/2004 | Original Date: | 09/24/2004 |
| Drug ID: | ALLEGRA-D TABLETS | DAW:N | Substitute: N |
| Manufacturer: | AVENTIS | Quantity: | 60 |
| Directions | TAKE ONE TABLET BY MOUTH TWICE DAILY | Qty Dispensed: | 60 |
| | | Drug Expiration | 09/24/2005 |
| Days Supply: | 30 Refills: 0 Refills Before: 09/24/2005 | Qty Remaining: | 0 |
| Prescriber: | KATHY KING Prescriber ID: AK1111119 | NDC: | 00088-1090-47 |
| Prescriber Phone: | (802) 849-6950 | | |

Event Recap

TESTING

Comment History

R 00 (Audit Tail) 10/01/2004 15:56:01:
Internal Events Added are: Same first name.

R AH 09/30/2004 16:33:07:
Rx 5 Rejected
need more data about prescription

Event Details

Drug Entered Into IC+: ALLEGRA-D TABLETS
Was the drug that was entered into IC+ the drug prescribed: Yes
Was the drug that was entered into IC+ the drug dispensed: Yes
Directions Entered Into IC+: TAKE ONE TABLET BY MOUTH TWICE DAILY
Was the directions that was entered into IC+ the directions prescribed: Yes
Was the directions that was entered into IC+ the directions dispensed: Yes

Root Cause Analysis for Incorrect Package in Patient

Confidential: Peer Review Document - DO NOT PRINT OR DUPLICATE

[ Reviewed ]   [ Cancel ]

3212

Contributing Factors

Refrigerated Item

Workstation Detail

| Station | Patient Entry (PE) | Script Entry (SE) | Filling (FILL) | Up-Front Verification (UFV) | Product Review (PR) | Out Window (OW) |
|---|---|---|---|---|---|---|
| Staff | ALYSSA KING | ALYSSA KING | | ALYSSA KING | ALYSSA KING | |
| Reviewed | No | No | | No | No | No |

Follow-up Actions

Patient Returned Incorrect Medication: No
Correct Medication give to Patient: No
Doctor Contacted: No
Refund Giver: No
Insurance Notified (per Supervisor): No
RXNet HPAA Disclosure form completed: Unknown
Incorrect prescription quarantined, Correct prescription filled for both patients: Unknown

Improvement Action Plan

TESTING

Confidential: Peer Review Document - DO NOT PRINT OR DUPLICATE

*FIG. 15E* — 3200

Comments:

Settlement Made: ⦿ Yes ○ No   Amount:

Check Payable to:   Check Dispatch Address:

Page Up | Page Down | Cancel

Submit to QA — 3224
Save as Draft — 3226
Reject — 3222
Extend Deadline — 3228

| Event is owned by | Queue Status | Store Queue | | | | | | District Queue | | | QA Queue |
|---|---|---|---|---|---|---|---|---|---|---|---|
| | | QA | RxS | DM | RxM | SM | Rph | QA | RxS | DM | QA |
| Store | Store Draft | Capture | Capture | Capture | Capture | Capture | Capture | | | | |
| Store | RxS Rejected | Capture | Capture | Capture | Capture | Capture | Capture | Inq/Rvw | Inq/Rvw | Inq/Rvw | |
| Store | Overdue to RxS | Inq/Rvw | Rxs Rvw | Rxs Rvw | Inq/Rvw | Inq/Rvw | Inq/Rvw | Rxs Xtnd | Rxs Xtnd | Rxs Rvw | Inq/Rvw |
| RxS | Submitted to RxS | Inq/Rvw | Rxs Rvw | Rxs Rvw | Inq/Rvw | Inq/Rvw | Inq/Rvw | Rxs Rvw | Rxs Rvw | Rxs Rvw | Inq/Rvw |
| RxS | RxS Draft | Inq/Rvw | Rxs Rvw | Rxs Rvw | Inq/Rvw | Inq/Rvw | Inq/Rvw | Rxs Rvw | Rxs Rvw | Rxs Rvw | Inq/Rvw |
| RxS | QA Rejected | Inq/Rvw | Rxs Rvw | Rxs Rvw | Inq/Rvw | Inq/Rvw | Inq/Rvw | Rxs Rvw | Rxs Rvw | Rxs Rvw | Inq/Rvw |
| RxS | Overdue to QA | Qa Rvw | Inq/Rvw | Inq/Rvw | Inq/Rvw | Inq/Rvw | Inq/Rvw | Qa Rvw | Inq/Rvw | Inq/Rvw | Qa Xtnd |
| QA | Submitted to QA | Qa Rvw | Inq/Rvw | Inq/Rvw | Inq/Rvw | Inq/Rvw | Inq/Rvw | Qa Rvw | Inq/Rvw | Inq/Rvw | Qa Rvw |
| QA | QA Draft | Qa Rvw | Inq/Rvw | Inq/Rvw | Inq/Rvw | Inq/Rvw | Inq/Rvw | Qa Rvw | Inq/Rvw | Inq/Rvw | Qa Rvw |
| QA | QA Filed | Qa Rvw | Inq/Rvw | Inq/Rvw | Inq/Rvw | Inq/Rvw | Inq/Rvw | Qa Rvw | Inq/Rvw | Inq/Rvw | Qa Rvw |

FIG. 16

| District Q | Store Q | Employee Q | New Event | Peer Review | Reports |
|---|---|---|---|---|---|
| | | | | | Logout |

District Reports

| | Trend | Summary | Detail |
|---|---|---|---|
| External Events | ET1, Stores<br>ET3, Pharmacist | ES1, Staff<br>ES2, Store by Type | |
| Internal Events | IT2, Stores | IS2, Stores and Stations<br>IS3, Pharmacist Capture Index | |
| Other Reports | | MPR CQI | |

District Reports

| | Trend | Summary | Detail |
|---|---|---|---|
| External Events | | | ED1, Detailed Data<br>ED2, Detailed including Stations |
| Internal Events | IT1, Stations in Store | IS1, Staff and Stations | ID1, Detail List |

INTEGRATED PHARMACY ERROR TRACKING AND REPORTING SYSTEM AND METHOD

CROSS-REFERENCE TO RELATED APPLICATIONS

None.

TECHNICAL FIELD

The present invention is related to a system and method for the capture, tracking, and quality improvement for errors which occur in a pharmacy operation. More particularly, the present invention relates to a system and method for efficiently capturing, tracking, analyzing, and providing continuous quality improvement in an integrated manner in relation to errors which occur in the distribution of medication to patients through a multi-store pharmacy operation.

BACKGROUND OF THE INVENTION

Patients commonly obtain their prescribed medications through pharmacies. One system used for delivering medications to patients is disclosed in U.S. Patent Publication No. 2004/0088187 A1, published May 6, 2004, to Chudy et al. The Chudy reference is directed to optimizing pharmacy workflow associated with fulfillment of prescription orders for medications and health related products in a pharmacy environment. The system coordinates and controls pharmacy workflow to sequence prescriptions for fulfillment in an attempt to make the process efficient and to minimize a cost function associated with fulfillment of the prescription order. The Chudy reference also specifies validating prescription orders. Computer program instructions are used for validating each prescription order at a work station, including steps of selecting a prescription from the prescription sequence presented on a display, reading machine-readable indicia on a label of a container corresponding to each selected prescription, and releasing the prescription only after agreement is reached between the readable indicia and prescription. Prior to releasing the prescription, the customer's medical records may be automatically searched to determine whether there are potential adverse drug interactions between the patient and the prescription(s). The Chudy reference fails to address tracking and/or evaluating errors after such errors have occurred.

One prior system did attempt to record errors which may have occurred in the prescription fulfillment process. When an error occurred in the order fulfillment process, a manual form was filled out at the local store. These forms were then sent to a centralized customer complaint center. At the centralized customer complaint center, the manual form was entered into a computer system, and certain information was recorded about each "case." The entering employee had the ability to create, modify, review and close a "case." The following information was manually entered onto a manual form and manually sent to the centralized customer care center: the name and address of the person identifying and notifying the pharmacy of the error, the patient name, address and contact information, date of notification, the prescription number, the responsible employee, the verifying pharmacist, the date the matter was resolved, whether the case is open or closed, an indication of whether the medication was returned, an indication of whether the person refused to return the medication, whether a refund was provided, the date of any refund, the amount of any refund, the identification of the correct medication, who created the "case," which store created the "case," the status of the case, the attitude of the person reporting the error, the date the prescription having the error was sold, an indication of whether counseling was provided, the date of any such counseling, whether any of the medication having the error was used, the date of the initial dose, how many doses were used, and the alleged condition of the patient. After manual entry, notes could be added about the event, about recommended improvements for involved employees, and about recommendations/comments manually received from a district supervisor. Directions were provided for documenting a case. Once manually entered at the centralized customer care center, cases could be searched by case number or other information, and for all cases for a particular store. Reports could be run at the centralized customer care center for cases by store and by employee. However, this system did not integrate the employees or systems of any of the stores with the centralized customer care center, did not integrate the active capture of events at the store level, did not integrate the ability to actively track and resolve each case, did not provide any feedback through the system from information garnered from the system, did not integrate supervisory feedback with employees involved in the events on an employee. store, district or other basis, did not integrate other store, district or corporate management level feedback, and did not provide automated tracking and administrative reporting of events to state and federal agencies.

One further prior system includes attempting to track all prescriptions for a sensitive drug, which is disclosed in U.S. Patent Publication No. 2005/0090425 A1, published Apr. 28, 2005, to Reardan et al. The system disclosed in Reardan attempts to track prescription abuses for sensitive drugs by tracking prescription patterns of doctors and patients. The number of product defects and complaints, the number of shipping errors, the number of returned products, the number of adverse events, and the number of dosing problems are shown in one or more reports. However, no further details are provided. Moreover, in the context of Reardan reference, at least some of this information relates to standard shipping issues, which are well known in the factory and warehouse distribution art, and which do not relate to automated pharmacy error tracking.

One additional prior system includes gathering, processing, storing and reporting pharmacy data, which is disclosed in U.S. Patent Publication No. 2004/0148195 A1, published Jul. 29, 2004 to Kalies. Data from individual pharmacies is transmitted regularly to a data repository via an electronic communications network. Data received at the data repository failing to meet certain criteria is rejected. If such data passes the criteria, it is accepted and added to the database. Users may request the data that is accepted in the database, after passing security checks on the users. The amount and types of data available to each user may be limited by the user's predetermined security level clearance in order to protect patient privacy. However, Kalies does not teach or suggest a pharmacy error event tracking and reporting system.

The present invention is provided to solve or address these and other problems.

SUMMARY OF INVENTION

The present system and method collects data about pharmacy error events within each pharmacy of a multi-store pharmacy system, for both internal pharmacy error events (caught in a pharmacy by pharmacy staff) and external pharmacy error events (caught after sale by the patient or patient's agent(s)). These error events affect at least pharmacy operations, supervision and quality assurance. In order to provide continuous quality improvement, various personnel at different levels need to get sufficient data and insights to proactively and systematically eliminate such error events. Detailed data collection mechanisms integrated into daily work flows allow for the appropriate and needed capture of error events in a manner which minimally impacts pharmacy fill operations, yet at the same time efficiently tracks and/or escalates these events when they occur to ensure that such events are being handled in an appropriate and timely manner. Flexible error event data analysis and reporting can be utilized in this continuous quality improvement process.

In one embodiment, a system and method is provided for integrating pharmacy error event tracking. The system has a first input device for receiving first error event data for a first pharmacy error event at a first pharmacy, a second input device for receiving second error event data for a second pharmacy error event at a second pharmacy, and a processor having a memory comprising a pharmacy error event database and a pharmacy error event tracking module. The processor, memory, pharmacy error event database, and pharmacy error event tracking module are configured to receive and store the first error event data and the second error event data, the pharmacy error event tracking module is configured to determine whether the first and/or second error event data require escalation, and the processor transmits a first and/or error event escalation message through a communication device to supervisory personnel in response to the determination. Thus, in the context of the above or other systems, the method steps include receiving first error event data for a pharmacy error event through a first input device at a first pharmacy, transmitting the first error event data to a pharmacy error event database associated with a first pharmacy error event computer, determining at the first pharmacy error event computer whether the first error event information requires escalation, and transmitting an error event escalation message through a communication device to supervisory personnel in response to the determining step.

In an additional embodiment in the context of the above and other systems, a further method is provided for integrated continuous quality improvement in reducing pharmacy error events. The method steps include receiving pharmacy error event data for each of a first plurality of pharmacy error events through one or more first input devices at a first pharmacy, transmitting the error event data for each of the first plurality of pharmacy error events to a pharmacy error event database within a pharmacy error event computer, tabulating the error event data with the pharmacy error event computer, wherein the tabulation is performed by a criteria for providing first insight information to supervisory personnel, transmitting the tabulated error event data through a communication device to the supervisory personnel in response to the tabulating step, and communicating the first insight information to first pharmacy personnel involved with the at least one of the first plurality of pharmacy error events.

In a further embodiment in the context of the above and other systems, a method is provided for integrated pharmacy error event data capture. The method steps include transmitting at least a portion of an input interface to a first input device at a first pharmacy, wherein the input interface provides a plurality of fields for inputting a plurality of pharmacy error event data, receiving the plurality of pharmacy error event data at a first error event computer, storing the plurality of error event data in a pharmacy error event database of the first error event computer, and, transmitting the plurality of error event data for an error event, stored in the error event database of the first error event computer, to a communication device for review by pharmacy personnel through the communication device.

Other features and advantages of the invention will be apparent from the following specification taken in conjunction with the following drawings.

BRIEF DESCRIPTION OF THE DRAWINGS

FIG. 6 is an interface screen of one embodiment of the system of FIG. 1 providing for entry of some pharmacy error event data and analysis information;

FIG. 9 is a further interface screen of one embodiment of the system of FIG. 1 providing for entry of some additional pharmacy error event data and analysis information;

FIG. 12 is an employee pharmacy error event interface screen of one embodiment of the system of Figure;

FIG. 13 is a peer review pharmacy error event interface screen of one embodiment of the system of FIG. 1;

FIG. 14 is a district supervisory review pharmacy error event interface screen of one embodiment of the system of FIG. 1;

FIG. 15(a) is a portion of an employee review pharmacy error event interface screen of one embodiment of the system of FIG. 1;

FIG. 15(b) is an additional portion of the employee review pharmacy error event interface screen of FIG. 15(a);

FIG. 15(c) is an additional portion of the employee review pharmacy error event interface screen of FIG. 15(a);

FIG. 15(d) is an additional portion of the employee review pharmacy error event interface screen of FIG. 15(a);

FIG. 15(e) is an additional portion of the employee review pharmacy error event interface screen of FIG. 15(a);

FIG. 15(f) is an additional portion of the employee review pharmacy error event interface screen of FIG. 15(a);

FIG. 16 is a table depicting available data and functions through various interfaces for various personnel at various stages of the processes within the system of FIG. 1;

FIG. 17 is a store and district report selection interface screen of one embodiment of the system of FIG. 1;

DETAILED DESCRIPTION

Figure 1:
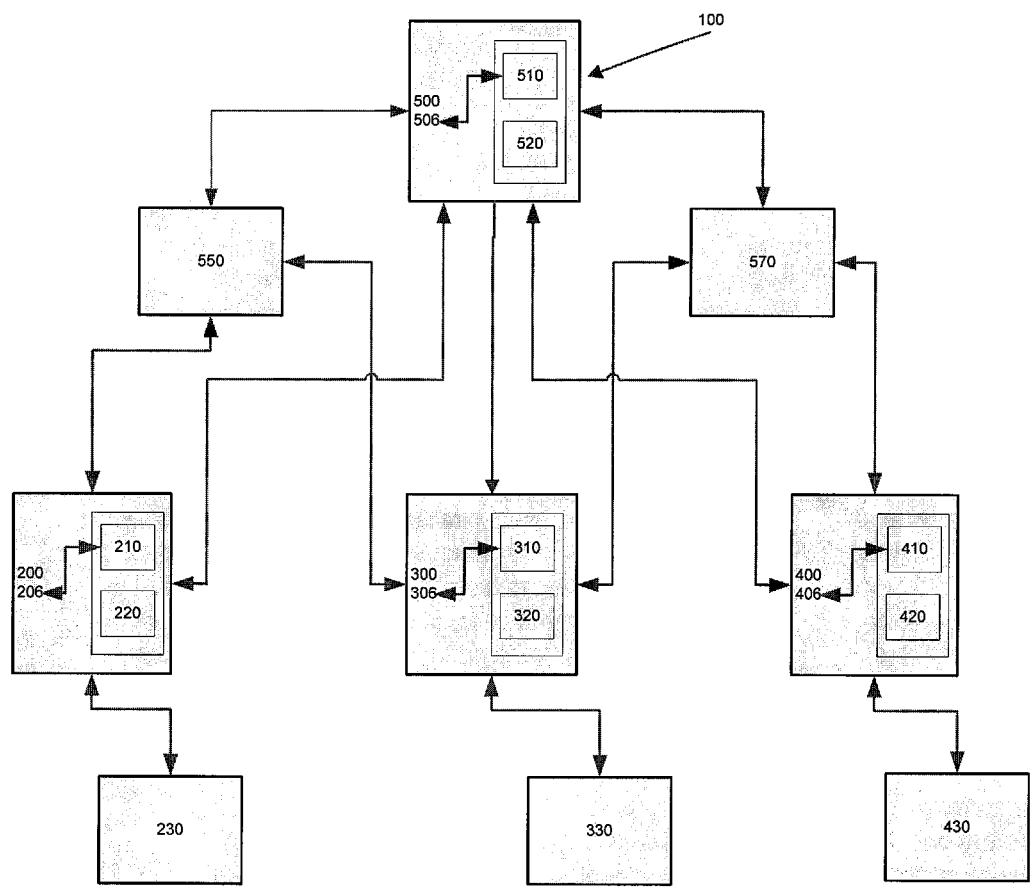
FIG. 1 is a schematic diagram illustrating one or more embodiments of a system of capture, tracking, and quality improvement for errors which occur in a single or multiple pharmacy store operation.

While this invention is susceptible to embodiment in many different forms, there are shown in the drawings and herein described in detail preferred embodiments with the understanding that the present disclosure is considered to provide an example of the principles of the invention, and is not intended to limit the broad aspect of the invention to the embodiments illustrated.

The "dispensing" of medication for a prescription involves entering, filling, verifying and selling the prescription including the medication. When a complaint for a prescription takes place, the complaint and possibly an error is analyzed and attempted to be prevented in the future. Specifically, any possible error is investigated as to how the event occurred, any factors that contributed to the event or other patients affected by the event is determined, and ways to prevent the event from happening in the future are sought out.

A pharmacy error event is any occurrence that prevents the pharmacy from filling any prescription correctly the first time, every time. A pharmacy error event might include such things as a prescription being somewhat unreadable requiring a call to the prescribing MD, or picking the wrong bottle from a shelf and then getting an automated or non-automated warning that the medication is wrong.

Referring to the drawings and initially to FIG. 1, there is shown a pharmacy error event system 100 for efficiently capturing, tracking, analyzing, and providing continuous quality improvement in an integrated manner in relation to errors which occur in the distribution of medication to patients through a single or multi-store pharmacy operation. As shown in FIG. 1, a single or multi-server based arrangement can be used to implement the system 100.

The pharmacy error event system 100 can be implemented in software running on various hardware platforms. A first pharmacy error event computer 200 can be provided for a first pharmacy store, a second pharmacy error event computer 300 can be provided for a second pharmacy store, and a third pharmacy error event computer 400 can be provided for a third pharmacy (can be many others). A district, corporate or central pharmacy error event computer 500 can be provided for centralizing error event data and/or for providing functionality which would otherwise be provided by the first, second and/or third pharmacy error event computers 200, 300, 400, as described in greater detail below. The first pharmacy error event computer 200 has a first processor and a first memory 206 having a first pharmacy error event database 210 and having first pharmacy error event software modules 220 for performing various pharmacy error event functions as will be described in greater detail below. The first pharmacy error event computer 200 is in communication with a first input device 230 (can be many others), such as a hand-held or desk-top computer terminal, which is located at the first pharmacy store, for receiving pharmacy error event data for pharmacy error events occurring at the first pharmacy or relating to prescriptions which have been filled or provided to patients through the first pharmacy. The first input device 230 transmits the pharmacy error event data for pharmacy error events relating to the first pharmacy to the first pharmacy error event computer 200 and to the first pharmacy error event database 210 for storage therein. Interface screens, described below, are displayed through the first input device for at least receiving the pharmacy error event data, and for other functions, which are provided at least in part by the pharmacy error event software modules 220 from the first error event computer 200. The first pharmacy error event computer 200 may be located at the first pharmacy or elsewhere.

The second pharmacy error event computer 300 has a second processor and a second memory 306 having a second pharmacy error event database 310 and having second pharmacy error event software modules 320 for performing various pharmacy error event functions as will be described in greater detail below. The second pharmacy error event computer 300 is in communication with a second input device 330 (can be many others), such as a hand-held or desk-top computer terminal, which is located at the second pharmacy store, for receiving pharmacy error event data for pharmacy error events occurring at the second pharmacy or relating to prescriptions which have been filled or provided to patients through the second pharmacy. The second input device 330 transmits the pharmacy error event data for pharmacy error events relating to the second pharmacy to the second pharmacy error event computer 300 and to the second pharmacy error event database 310 for storage therein. Interface screens, described below, are displayed through the second input device for at least receiving the pharmacy error event data, and for other functions, which are provided at least in part by the pharmacy error event software modules 320 from the second error event computer 300. The second pharmacy error event computer 300 may be located at the second pharmacy or elsewhere. Likewise, the third pharmacy error event computer 400 has a third processor and a third memory 406 having a third pharmacy error event database 410 and having third pharmacy error event software modules 420 for performing various pharmacy error event functions as will be described in greater detail below. The third pharmacy error event computer 400 is in communication with a third input device 430 (can be many others), such as a hand-held or desk-top computer terminal, which is located at the third pharmacy store, for receiving pharmacy error event data for pharmacy error events occurring at the third pharmacy or relating to prescriptions which have been filled or provided to patients through the third pharmacy. The third input device 430 transmits the pharmacy error event data for pharmacy error events relating to the third pharmacy to the third pharmacy error event computer 400 and to the third pharmacy error event database 410 for storage therein. Interface screens, described below, are displayed through the third input device for at least receiving the pharmacy error event data, and for other functions, which are provided at least in part by the pharmacy error event software modules 420 from the third error event computer 400. The third pharmacy error event computer 400 may be located at the third pharmacy or elsewhere.

As mentioned, the district, corporate or central pharmacy error event computer 500 can be provided for centralizing error event data and/or for providing functionality which would otherwise be provided by the first, second and/or third pharmacy error event computers 200, 300, 400 (can be many others). Specifically, the district, corporate or central pharmacy error event computer 500 has a central processor and a central memory 506 having a central pharmacy error event database 510 and having central pharmacy error event software modules 520 for performing various pharmacy error event functions as will be described in greater detail below. In one embodiment, the central pharmacy error event computer 500 is in communication with the first, second, and/or third pharmacy error event computers 200, 300, 400 for centralizing all or part of the pharmacy error event data received and stored at such computers 200, 300, 400. The pharmacy error event data can then be reviewed, tracked, reported, analyzed, etc. on a cumulative and other global basis from supervisory terminal devices 550, 570, which can for example be a handheld or desk-top computer, as will be described in further detail below. Alternatively, the central pharmacy error event computer 500 can be directly in communication with first, second, and third input devices 230, 330, 430 (can be many others) for receiving pharmacy error event data for pharmacy error events occurring at the various pharmacies where the input devices 230, 330, 430 are located, or relating to prescriptions which have been filled or provided to patients through various pharmacies within a multi-store pharmacy enterprise. The input devices 230, 330, 430 transmit the pharmacy error event data for pharmacy error events to the central pharmacy error event computer 500 either directly or through other computers or systems, and to the central pharmacy error event database 510 for storage therein. Interface screens, described below, are displayed through the input devices 230, 330, 430 and through supervisory interface devices 550, 570 for at least receiving the pharmacy error event data, and for other functions, which are provided at least in part by the pharmacy error event software modules 520 from the central error event computer 500. In one embodiment, the central pharmacy error event computer 500 is located remotely from the pharmacies, and at the corporate or enterprise main offices.

As generally indicated, the system 100 can be implemented in the context of FIG. 1 or other configurations, in software, as an executable program(s), such as through the software modules 220, 320, 420, 520 including the interface modules therein, executed by one or more special or general purpose digital computer(s), such as a personal computer (PC; IBM-compatible, Apple-compatible, or otherwise), personal digital assistant, workstation, minicomputer, server, or mainframe computer.

As mentioned, in terms of hardware architecture shown in FIG. 1, one or more of the mentioned computers 200, 300, 400, 500 and input devices 230, 330, 430, 550, 570 can include a processor, memory, and one or more input and/or output (I/O) devices 306 (or peripherals) that are communicatively coupled via a communication interface. The communication interface can be, for example, but not limited to, one or more buses or other wired or wireless connections, as is known in the art. The communication interface may have additional elements, which are omitted for simplicity, such as controllers, buffers (caches), drivers, repeaters, and receivers, to enable communications. Further, the interface may include address, control, and/or data connections to enable appropriate communications among the other computer components.

The processors are hardware devices for executing software, particularly software stored in memory, such as memory 206, 306, 406, 506. The processor can be any custom-made or commercially available processor, a central processing unit (CPU), an auxiliary processor among several processors associated with the computers 200, 300, 400, 500 and input/interface devices 550, 570, a semiconductor-based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc., or a 68xxx series microprocessor from Motorola Corporation. The processors may also represent a distributed processing architecture such as, but not limited to, SQL, Smalltalk, APL, KLisp, Snobol, Developer 200, MUMPS/Magic.

The memory 206, 306, 406, 506, and other memories, can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory may incorporate electronic, magnetic, optical, and/or other types of storage media. The memory can have a distributed architecture where various components are situated remote from one another, but are still accessed by the processors.

The pharmacy error event software 220, 320, 420, 520 in respective memory 206, 306, 406, 506 may include one or more separate programs or modules. The separate programs comprise ordered listings of executable instructions for implementing logical functions. In the example of FIG. 1, the software in memory, including memory of I/O devices 230, 330, 430, 550, 570, also includes a suitable operating system (O/S). A non-exhaustive list of examples of suitable commercially available operating systems is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run-time Vxworks operating system from WindRiver Systems, Inc.; or (g) an appliance-based operating system, such as that implemented in handheld computers or personal digital assistants (PDAs) (e.g., PalmOS available from Palm Computing, Inc., and Windows CE available from Microsoft Corporation). The operating system essentially controls the execution of other computer programs, such as the pharmacy error event software 220, 320, 420, 520 of system 100, and provides scheduling, input-output control, file and data management, memory management, and communication control and related services.

The pharmacy error event software 220, 320, 420, 520 of system 100 may be a source program, executable program (object code), script, or any other entity comprising a set of instructions to be performed. When a source program, the program needs to be translated via a compiler, assembler, interpreter, or the like, which may or may not be included within the memory, so as to operate properly in connection with the O/S. Furthermore, the pharmacy error event software 220, 320, 420, 520 of system 100 can be written as (a) an object-oriented programming language, which has classes of data and methods, or (b) a procedural programming language, which has routines, subroutines, and/or functions, for example but not limited to C, C++, Pascal, Basic, Fortran, Cobol, Perl, Java, and Ada. In one embodiment, the pharmacy error event software 220, 320, 420, 520 of system 100 is written in C++, Java and/or html for use with client type I/O devices.

The I/O devices may include input devices, for example but not limited to a keyboard, mouse, scanner, microphone, touch screens, interfaces for various communications devices, barcode readers, stylus, laser readers, radio-frequency device readers, etc. Furthermore, the I/O devices may also include output devices, for example but not limited to a printer, barcode printers, displays, etc. Finally, the I/O devices may further include devices that communicate both inputs and outputs, for instance but not limited to a modulator/demodulator (modem; for accessing another device, system, or network), a radio frequency (RF) or other transceiver, a telephonic interface, a bridge, and a router.

Figure 3:
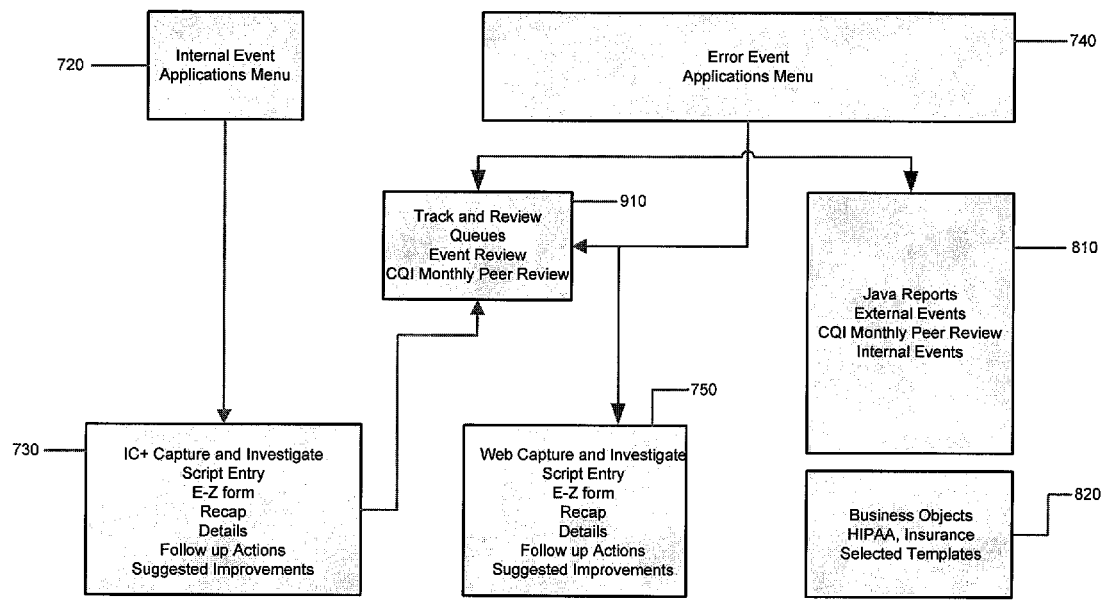
FIG. 3 is a further functional flow diagram of functional modules of an embodiment which can be implemented within the system of FIG. 1.

If the computer 200, 300, 400, 500 and/or I/O devices 230, 330, 430, 550, 570 is a PC, workstation, PDA, or the like, the software in the memory may further include a basic input output system (BIOS) (not shown in FIG. 3). The BIOS is a set of essential software routines that initialize and test hardware at startup, start the O/S, and support the transfer of data among the hardware devices. The BIOS is stored in ROM so that the BIOS can be executed when the computer is activated.

When computer 200, 300, 400, 500 is in operation, the respective processors are configured to execute software stored within memory 206, 306, 406, 506, to communicate data to and from memory 206, 306, 406, 506, and to generally control operations of the computer(s) 200, 300, 400, 500, pursuant to the software. The pharmacy error event software 220, 320, 420, 520 of system 100, and the O/S, in whole or in part, but typically the latter, are read by processor(s), perhaps buffered within the processor, and then executed.

It should be noted that pharmacy error event software 220, 320, 420, 520 can be stored on any computer-readable medium for use by or in connection with any computer-related system or method. In the context of this document, a computer readable medium is an electronic, magnetic, optical, or other physical device or means that can contain or store a computer program for use by or in connection with a computer related system or method. The pharmacy error event software 220, 320, 420, 530 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable media would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Figure 2:
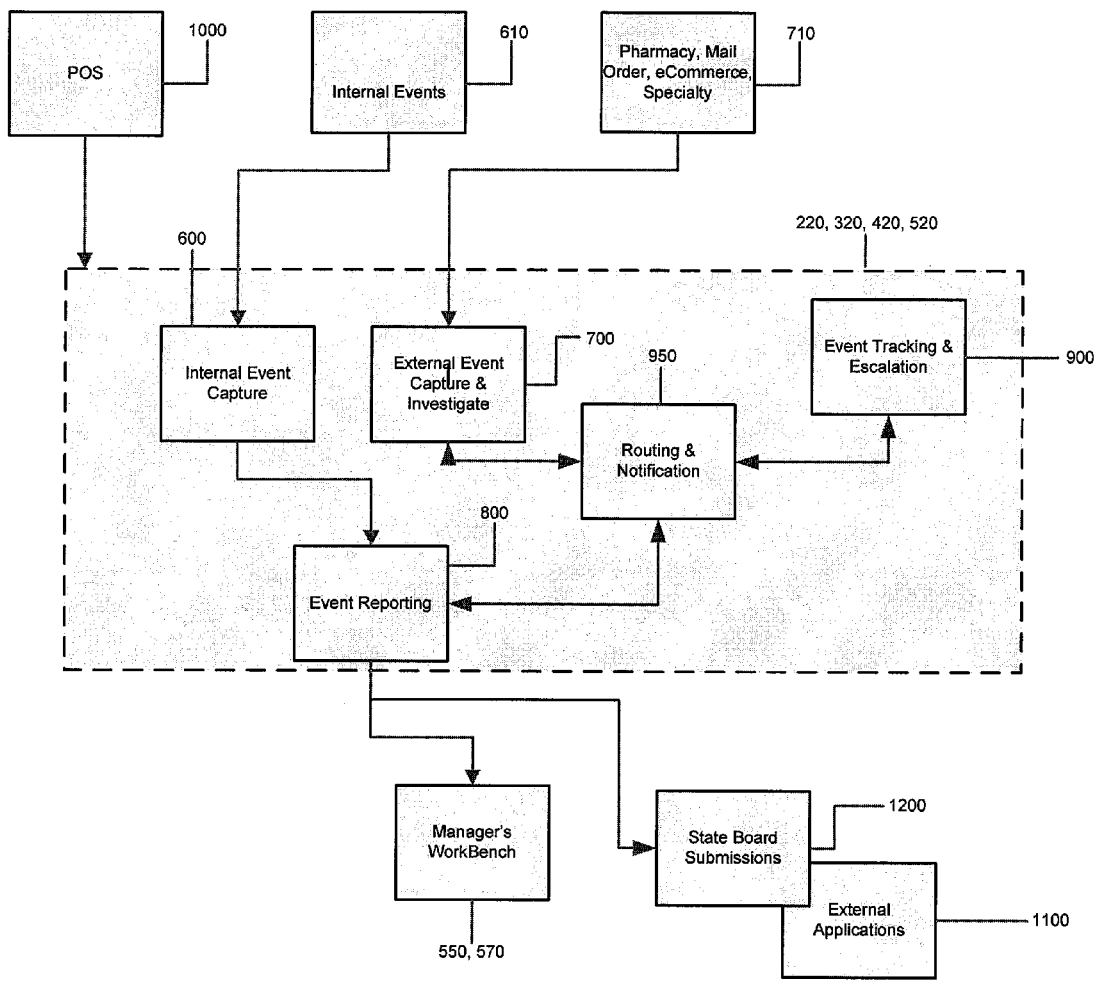
FIG. 2 is a functional flow diagram of functional modules of an embodiment which can be implemented within the system of FIG. 1.

Returning additionally to FIG. 2, the pharmacy error event software 220, 320, 420, 520 of system 100 has an internal error event capture module 600, an external error event capture and investigation module 700, an event reporting module 800, and an event tracking and escalation module 900 and a routing and notification module 950. Internal error event data 610 is entered through input devices 230, 330, 430 with the use of functionality provided by the internal error event capture module 600. The internal error event data 610 comes from the pharmacies and is entered through the input devices 230, 330, 430. External event data 710 and other investigative information is entered through input and interface devices 230, 330, 430 with the use of functionality provided by the external error event capture and investigation module 700. The external error event data 710 can come from various sources, depending on how a prescription was provided to a patient, such as from a pharmacy, as well as from mail order prescription means, eCommerce prescription means, or specialty item prescription delivery means, as indicated in FIG. 2. Each such source of external "pharmacy" error events can be entered through input devices such as input devices 230, 330, 430, from such other facilities. Error events reports, including tabulation of the error event data, can be reported to the various input and interface devices 230, 330, 430, 550, 570 with the use of functionality provided by the error event reporting module 800. Error events can be tracked and escalated through the use of the various input and interface devices 230, 330, 430, 550, 570 and the functionality provided by the error event tracking and escalation module 800. Prescription information, including the patient name, prescription, prescription instructions, etc. can be directly received from a point of sale (POS) system 1000 into the various modules 600, 700, 800, 900 for use in creating and modifying error event records, as well as for at least viewing and reporting such prescription information. Error event data, records, reports, and other information can be electronically sent from pharmacy error event software 220, 320, 420, 520 of system 100 through the error event reporting module to external applications 1100, through electronic communications interfaces, such as to an insurance carrier which may have provided insurance coverage for such error events. Error event data, records, reports, and other information can also be electronically sent from pharmacy error event software 220, 320, 420, 520 of system 100 through the error event reporting module to State/Federal Boards 1200, which may be required by a state and/or federal regulations, through electronic communications interfaces. Sending error events to external applications 1100, such as to insurance carriers and/or to Boards 1200, may be required in certain circumstances for certain types of error events having criteria or properties satisfying certain predetermined criteria or properties, such as for example hospitalization of a patient allegedly being caused as a result of the error event occurring.

Referring additionally to FIG. 3, one embodiment of pharmacy error system 100 is shown in a functional flow diagram. Specifically, pharmacy error event system software 220, 320, 420, 520 provides an internal event applications menu and module 720 through which various capture and investigate functions are provided. This menu 720 allows personnel to choose from at least the following capture and investigate interface screens 730: a prescription information ("script") entry interface screen, an "easy" or E-Z form interface screen to enter information relating to an error event, a recap interface screen, a details interface screen for entry of additional details of an error event, a follow-up actions interface screen for follow-up actions which may be needed or appropriate for an error event, and a suggested improvements interface screen for suggesting to personnel ways to reduce the quantity and quality of pharmacy error events and continuously improve quality. These capture and investigate interface screens and module 730 are provided at the pharmacy level, and in one embodiment are not formatted for use with internet browsers, although these interfaces may be formatted in such a manner. The capture and investigate module 730 provides various capture and investigation functionality, as will be explained below. Error event data and information which is received through these capture and investigate interface screens 730 (through input devices 230, 330, 430) may be viewed and used through a main error event applications menu 740, and in particular through track and review interface screens and module 910. Error event data and information which is received through these capture and investigate interface screens 730 are effectively captured, tracked and analyzed by the track and review interface module 910. The track and review interface screens and module 910 include various "queue" interface screens or "queues," event review interface screens, as well as continuous quality improvement interface peer review interface screens (monthly or some other time interval). The track and review module 910 also receives internal error event data and information from module 730 for tracking and review functions to be applied to such internal error event data and information. "Web" capture and investigate interface screens 750 are also available through the error event applications menu 740, which provide similar functionality as the capture and investigate interface screens 730, but which are directed to capturing and investigating external error events and other functions, and are available through a web browser, through the interface devices 230, 330, 430, 550, 570 and other devices. In one embodiment, the creation of an event record through the capture and investigate modules 730, 750 can only be done at a pharmacy. Report interface screens and module 810 are also available through the error event application menu 740, including at least external event report interface screens, continuous quality improvement report interface screens, internal error event report interface screens, and other functionality, as will be described below. These report interface screens and modules can be programmed in Java for utilizing scripts and other internet/browser-based interface functions available through this programming language. Error event data, records, and information can be reported to external systems and destinations through templates utilizing a "BusinessObjects" module 820. These interface screens will be described in greater detail below.

Routing and hierarchy of access to information for event notification and escalation can be derived from position codes, roles, and location of personnel of the pharmacy and pharmacy enterprise. A detailed organizational hierarchy can be stored and utilized for these and other functions within one of more of the pharmacy databases 210, 310, 410, 510, or within the POS system 1000 for use within the pharmacy error event system 100. There are various different players or personnel in a pharmacy and in a pharmacy enterprise or organization. At each pharmacy store, there are one or more technicians (Tx or Tech) who receive prescriptions, enter prescriptions into the POS system 1000, pick prescriptions, and fill prescriptions. Each pharmacy also has one or more pharmacists (Rx) who also are involved with prescription filling, at least in checking the accuracy of the filling of the prescription before being provided to the patient. One or more Figures of the present specification may indicate either one of both of the technician and/or store pharmacist as "RPh" A store manager (SM) and a pharmacy supervisor (RxS) are additional personnel within each pharmacy store. Pharmacy supervisors (RxS) can also be "located" at the district level. A district manager (DM) or pharmacy supervisor (RxS) can be responsible for two or more stores which can be classified as a district. Regional managers (RM) can also be involved in the process described herein and are responsible for two or more districts which make up such region. Quality assurance (QA) and/or personnel at the corporate level are responsible for all of the regions, districts, and stores and are also involved in the process described herein.

Computer systems, such as POS system 1000, are utilized throughout the process. Thus, at least some manual checking of whether a prescription order has been correctly filled is performed, and in some pharmacies and pharmacy enterprises, some automated checking of whether a prescription order has been correctly filled is performed. The system 100 can include such automated checking functionality and interface screens. However, even with such manual and automated checking in place, some pharmacy error events (internal and external) will and do occur. For example, the system 100 and pharmacy error event software 220, 320, 420, 520 and modules therein can provide automatic internal error event capture as prescriptions are entered and filled in a pharmacy using keystroke capture and analysis, and using other mechanisms, as will be described below. Thus, internal and external error event capture, tracking, analysis, feedback and reporting occurs through the interactions of at least the above-mentioned personnel with the system 100.

On a daily basis, each pharmacy dispenses prescriptions, responds to customer issues through appropriate procedures, captures external error events, investigates the causes or the error events, follows up as necessary for such error events. The pharmacy supervisor and quality assurance electronically receive such error event data and information. Pharmacy staff review at least the external error events they were involved in, and a peer review occurs with the use of the tracked results through the system 100 on a time interval basis such as on a monthly basis. At the store pharmacy level on a daily basis, the system 100 tracks and captures internal error events as they occur during the dispensing process from behind the scenes, and captures and investigates external error events. At the store and district level, periodic reporting and analysis occurs through the use of web-based standardized reports, which has a variety of filters (e.g. particular drug, employee or pharmacy station).

Daily functions at the district level include tracking events, especially those error events that have not been resolved. The district level personnel review the electronic error event data and investigation information electronically provided by the pharmacy store. The reviewed error event data or record is either forwarded to QA, or the district level personnel rejects such error event with comments through the interface screens of the system 100 and returns the error event record to the pharmacy store for completion of the error event data record and investigation through the system 100. The district-level supervisor can extend the time allowed to complete an event record through the interface screens of the system 100, within predetermined quality assurance criteria or limits. The district-level supervisor can also reassign an error event record to another store through the interface screens of the system 100. In one embodiment, the pharmacy supervisor who does an investigation on an error event record must go to a pharmacy store to use the capture interface screens. In such an embodiment, the pharmacy supervisor cannot update an error event record in the district and can only pass comments back to the pharmacy or forward the error event record to the corporate quality assurance personnel. At the district and corporate levels, the system 100 provides for tracking, reviewing and escalation of error events, and includes at least the capabilities of automatically escalating error events that have not been resolved.

At the corporate level on a daily basis, corporate supervisory personnel review external event records and data through the use of the system 100. The corporate supervisory personnel either files the error event record or rejects the error event record and returns it with comments to pharmacy supervisor at the district level for further action, through the use of the system 100. The corporate supervisory personnel can extend the time allowed to complete an error event record capture and investigation, and can reassign an error event record to another pharmacy supervisor for further processing, through the system 100. The system 100 also allows certain corporate supervisor personnel "power users" to conduct special analyses and/or define new standard reports for users of the system 100, through the system 100.

As mentioned above, internal error events can be captured and logged by using automated interface screens, such as for example visual checking, barcode/identifier checking, and weight checking interface screens and functionality. Internal events can also be entered through standard capture interface screens. A verifying pharmacist and/or a technician will enter, capture or otherwise "log" internal error events as follows: A patient or some representative comes to or contacts the pharmacy. They give the technician located at the pharmacy window their identifying information and the hard copy of the prescription (if they are in the pharmacy). The technician opens up "patient inquiry" in order to find and select the correct patient with the use of the "script" interface screens of capture and investigate module 730. If the patient does not exist, then the technician registers the new patient. The technician fills out "script" entry with the information on the hard copy. The filling technician can use the system 100 to print the prescriptions, such as labels for the prescription to put on containers. The filling technician finds the drug and fills the prescription.

As one check, first, the technician scans the prescription label barcode, then the barcode on the drug pack from which the prescription will be filled. If barcodes do not match, the input/interface device 230, 330, 430 of the system 100 will display a "mismatch" message. The technician dumps out the pills and hits enter on the keypad to check the amount. As an additional check, the technician can use a scale (not shown) interfaced with and a part of the system 100 to check if the weight of the filled prescription matches (within certain predetermined tolerances) the weight which the database has stored for such prescription. Once any needed corrections are made, the system 100 will respond with a successful verification message or an invalid quantity message (if not properly corrected). After successfully filling the prescription, the label and bottle go into a tote container and to a "verification" stage or staging area (or both). At the verification stage, the pharmacist checks the hard copy label and the prescription information in the system 100 database(s) or from the POS system 100 interfaced with the system 100. The pharmacist also visually compares the product in the vial with the label. At the "out window" of the pharmacy, the patient arrives and the technician greets them, prompting for their name and address and matching it to the bag. The technician may offer counseling from the pharmacist (technician may counsel patient, depending on state), and complete the sale on the register.

The "script" interface screens from the capture and investigate module 730 are where some internal error events can be captured. Specifically, hand written prescriptions can be electronically scanned into the system 100 or interfaced systems, such as POS system 1000. First, illegible writing can occur when the image scan is acceptable and the handwriting may be too difficult to transcribe. Second, missing information can occur when the scan and handwriting is acceptable, but the prescriber did not include important information, such as drug strength and/or directions. The following table sets out error events that can be captured in the system 100 for these circumstances, and which can be selected from a listing of error events for the pharmacist and/or technician to choose from.

| Name | External Event | Internal Event | Reason |
| --- | --- | --- | --- |
| Image - Problem With Image | Incorrect Drug | Was handwriting illegible? | Illegible Writing |
| Image - Missing Information | Incorrect Strength | Missing or omitted information? | Missing Information |

When the pharmacist is reviewing the prescription through a "data review" interface screen, internal events can be captured by trapping mouse clicks on the existing buttons of the interface. In order to capture more details about the specific type of internal event, a drop-down menu, icon or other interface tool can allow a user (pharmacist) to select or type the Incorrect Drug Name, Incorrect Strength, Incorrect Dosage Form, Incorrect Manufacturer, Incorrect (patient) Name, Incorrect Date of Birth, Incorrect Address, and/or Incorrect Phone to indicate one of more types of error events which the pharmacist caught during the review. The following table sets out some of the types of error events which the system can capture.

| Name | External Event | Internal Event |
| --- | --- | --- |
| Drug | Incorrect Drug | Was drug entered incorrectly? |
| Drug Name | Incorrect Drug Name | How was drug picked? |
| Drug Strength | Incorrect Strength | Was incorrect strength entered? |
| Drug Dosage Form | Incorrect Drug Dosage Form | Was it in incorrect dosage form? |
| Drug Manufacturer | Incorrect Drug Manufacturer | Incorrect Manufacturer? |
| Name (entry) | Incorrect Patient | Was patient entered incorrectly? |
| Name (actual) | Incorrect Patient Name | Was name incorrect? |
| Name - DOB | Incorrect Patient DOB | Was DOB incorrect? |
| Name - Phone | Incorrect Patient Phone | Was phone incorrect? |
| Name - Address | Incorrect Patient Address | Was address incorrect? |
| Name (Prescriber) | Incorrect Prescriber | Was prescriber entered incorrectly? |
| Directions | Incorrect Directions | Were directions entered incorrectly? |
| Quantity | Incorrect Quantity | Was quantity entered incorrectly? |
| Refills | Incorrect Refills | Was incorrect number of refills entered? |

Other error event data, such as quantity dispensed, days supply, DAW, original date, refills before, or any other data which could be important to why an error event might occur can be captured in this process.

When the pharmacist is reviewing "drug utilization" through a drug utilization review interface screen, error events can be captured by trapping mouse clicks on the existing buttons of the interface or through the interface in other ways. Specifically, the system 100 can capture when the pharmacist overrides DURs ("drug usage review" warnings) when there is an external event captured.

| Field Name | External Event | Internal Event |
|---|---|---|
| Override or Override All | Incorrect Directions | DUR/Dosage override? |
| Override or Override All | Adverse Drug Reaction | DUR Dosage override? |

As mentioned above, error events can occur when the "check weight" procedure is being performed. When the product has a barcode, the technician will use the scale by first scanning the barcode. If there is a mismatch, the scale will display some form of a "mismatch" message, and an error event entry or record will be inserted into the error event database 210, 310, 410, 510. If the scale has a piece-weight for the product, the technician will count out the pills by pouring them into the scale's measuring cup. When the technician measures out the number of pills and then tries to check it again with the scale, if the quantity is wrong, the scale will display an "invalid quantity" message, and an error event entry or record will be inserted into the error event database 210, 310, 410, 510. Among other associated information such as what personnel was logged into the computer at the time, what patient the prescription was for, etc., the database will keep track of how many times a mismatch was found on the fill The following table indicates the error events which can be captured for this situation.

| Field Name | External Event | Internal Event |
|---|---|---|
| Invalid Qty | Incorrect Quantity | Did the weight check report an incorrect quantity? |
| Mismatch | Incorrect Drug | Did the weight check report an incorrect drug? |

If for some reason, the filling technician does not complete the filling process using the weight check process, a message can appear during the review process requiring the pharmacist to give a reason why the scale was not used. The following are the types of reasons that can be provided or selected at the interface screen within the system 100.

| Field Name | External Event | Internal Event |
|---|---|---|
| Broken | Incorrect Drug | Broken |
| No Barcode | Incorrect Drug | No barcode |
| Patient Wanted Orig. Container | Incorrect Drug | Patient wanted original container |
| Incorrect Barcode or Piece weight | Incorrect Drug | Incorrect barcode or piece weight |

During the product review by the pharmacist using the product review or data review interface screens, a selection can be provided to select a reason for rejecting the fill. The following, and other, choices can be provided.

| Field Name | External Event | Internal Event |
|---|---|---|
| Reject | Incorrect Drug | Was it filled incorrectly? |
| Reject - Drug Name | Incorrect Drug Name | Was it filled incorrectly? |
| Reject - Strength | Incorrect Strength | Was incorrect strength filled? |
| Reject - Manufacturer | Incorrect Drug | Incorrect Manufacturer? |
| Reject - Dosage Form | Incorrect Drug | Was it an incorrect Dosage? |
| Reject - Label | Incorrect Label | Was it labeled incorrectly? Was incorrect label placed on incorrect vial? |

The listing of external error events in the above tables indicates that the error events can be caught external to the pharmacy, in which case the error event will be an external error event instead of an internal error event. The error event data or information is similar and used in a similar manner, as will be explained below, only entered into the system at a different time, and through different interface screens.

Figure 4:
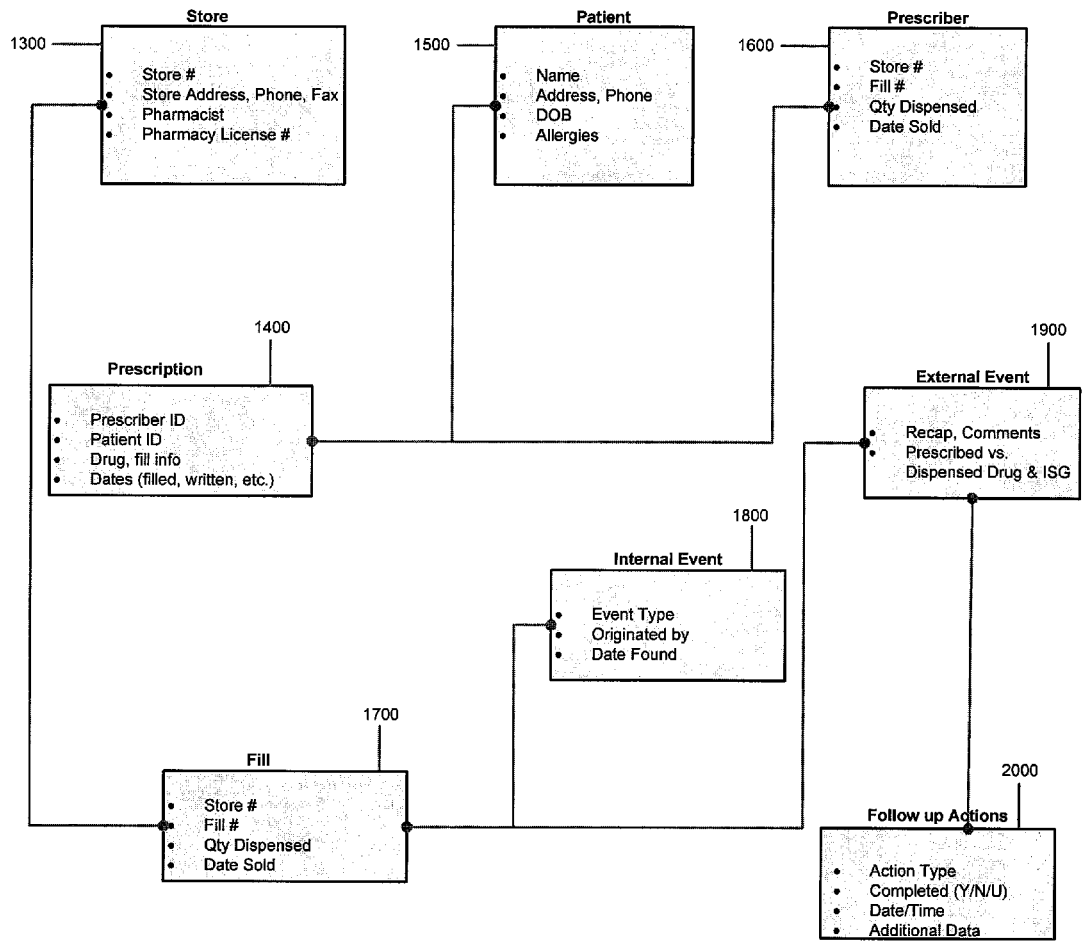
FIG. 4 is a diagram of one relational database structure for the system of FIG. 1.

Referring additionally to FIG. 4, one embodiment of at least a portion of the pharmacy error event database 210, 310, 410, 510 is shown in a relational database format. Specifically, at least pharmacy store data 1300, prescription data 1400, patient data 1500, prescriber data 1600, fill data 1700, internal error event data and records 1800, external error event data and records 1900, follow-up actions data 2000, and other data and information are stored in the pharmacy error event database 210, 310, 410, 510, in a relational structure as shown, as one of ordinary skill in the art would understand. In one relational structure, pharmacy store data 1300 comprises pharmacy store #, store address, phone number, fax number, e-mail/other contact information, pharmacist, and pharmacy license #. Prescription data 1400 comprises prescriber ID, patient ID, drug and fill information, and dates (filled, written, etc.). Patient data 1500 comprises name, address, phone, DOB (date of birth), and allergies. Prescriber data 1600 comprises pharmacy store #, fill #, quantity dispensed, and date sold. Fill data 1700 comprises store #, fill # quantity dispensed, and date sold. Internal error event data and records 1800 comprises event type, originated by, and date found. External error event data and records 1900 comprises event type, recap and comment information, and prescribed verses dispensed drug and SIG. Follow-up actions data 2000 comprises action type, completed status, date and time, and additional data. This relational structure allows for capture, investigation, tracking, and reporting of this and other information and data as understood from the other figures and above/below description.

As mentioned, for internal error events, the pharmacist verifies a prescription using a verification process. During this verification process, any internal error events are trapped or automatically captured by the system 100 as such error events occur during the pharmacy filling process. The automatic capture process will also transfer these error events to the database tables shown in FIG. 4 (to the error event database 210, 310, 410, 510) for reporting and analysis, as explained above. External error events are captured using the event capture user interfaces. The captured event is investigated, and the investigation information is stored in the error event database 210, 310, 410, 510 database as well. When an external event is reported, all related error event data and information is gathered and entered into the system from where the prescription was filled. The error event data is then submitted for further review by a pharmacy supervisor and quality assurance personnel. These and other related steps will also be explained below in the context of interface screens of the pharmacy error event system 100 for implementing this and other functionality.

Figure 5:
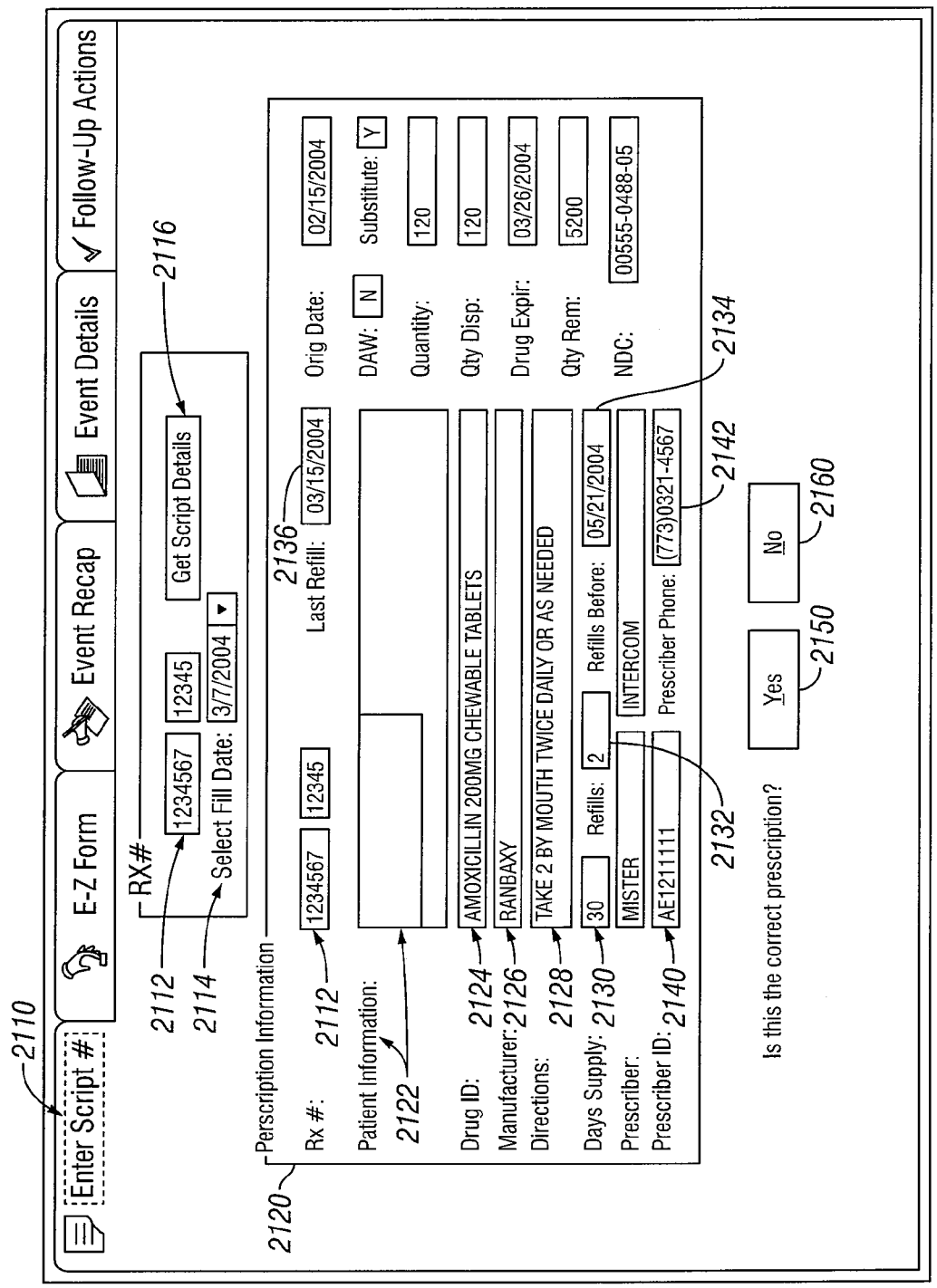
FIG. 5 is an interface screen of one embodiment of the system of FIG. 1 providing for entry and/or referencing pharmacy prescription data information.

Besides the particular interface screens used to fill and deliver prescriptions to patients discussed above, as mentioned above, various interface screens are provided by the system 100 and by the error event system software 220, 320, 420, 520 for specifically entering and capturing error event data relating to error events. Once error events are reported (external) or determined (internal), an error event record is created through the input device 230, 330, 430 located at the particular pharmacy where the technician and/or pharmacist is working. Referring additionally to FIG. 5, a prescription or "script" entry interface screen 2100 is shown. In this embodiment, the interface screen 2100 is entitled "Enter Script#," which can be selected by "clicking" on the "Enter Script#" tab 2110. The Enter Script interface screen 2100 allows a pharmacist or technician to capture basic, initial error event data information regarding an error event. The prescription number "RX#" 2112 is entered by the user, and the enter button of the input device 230, 330, 440 or get details button 2116 can be pressed. The fill date 2114 (which can be selected from a calendar) is also entered by the user to verify the date. By pressing the details button 2116, information in the "Prescription Information" box 2120 can be automatically filled in by the capture module of the pharmacy error event software by requesting such data from the POS system 1000 or from within the error event database 210, 310, 410, 510. This information can be entered manually as well, instead of being automatically populated. The information populated or manually entered appears in RX# field 2112, patent information field 2122 (patient name, address, phone number, e-mail address, etc.), drug identification field 2124, manufacturer (of the drug) field 2126, directions (for taking the drug) field 2128, days supply field 2130, refills field 2132, refills before field 2134 (no refills after date), last refill date field 2136, prescriber name field 2138, prescriber ID field 2140, prescriber phone number field 2142, and respective data therein, and other fields and information associated with the prescription as shown in FIG. 5. The user is requested to selected whether the prescription information is correct. By clicking on the "Yes" button 2150 at the bottom of the "Prescription Information" box 2120, the input device 230, 330, 430, 530 will take the user to a data entry form or interface screen 2200, as shown in FIG. 6. When the "Yes" button 2150 is pressed, the basic information regarding the error event from the prescription entry interface screen 2100 is recorded in the external event table 1900 of the error event database 210, 310, 410, 510 shown in FIG. 4. If the "No" button 2160 is chosen, then the Prescription Information box 2120 is cleared, and the user may enter a new RX#2112 and fill date 2114 to find the correct prescription. The user may also manually enter this information. If an error event record has already been established for the error event related to the prescription number or identifier, after entering an RX#2112, the system will provide a message that an error event record has already been established, and the system will ask the user if they would like to edit or review the existing event record. If the answer is no, then nothing further will happen, and the user must enter a different prescription number. If the answer is Yes, then the error event capture module will open to the existing event, displaying the "Event Recap" interface screen shown in FIG. 7, which will be described below.

Referring additionally to FIG. 6, an error event data entry form or interface screen 2200 is shown. In this embodiment, the interface screen 2200 entitled "EZ-Form" appears after entering the prescription information in the prescription entry interface screen 2100 of FIG. 5. Alternatively, an "open" or "rejected" error event record can be selected from another interface screen, such as for example a "store queue" or store interface screen. As an additional embodiment, the "EZ-Form" tab 2210 could be selected. Other tabs are shown and the screens associated therewith, which will be described below. The EZ-Form 2200 allows a technician or pharmacist to enter or capture all data necessary for quality assurance acceptance of the error event, in an ongoing fashion. When this interface screen appears, all previously entered data regarding the error event is pre-populated and displayed. Any empty field can be entered and automatically populated, or previously entered information can be modified. The user is asked to enter an event type in an event type field 2215, answer whether the medication was used by selecting a yes or no field 2220, enter how many doses were used in doses used field 2225 or click an "unknown" box, enter the patient's alleged health condition in a patient's alleged health condition field 2230, and enter the patient's alleged attitude in a patient's alleged attitude field 2235. Pre-populated choices can be included in the above information for capturing event type, patient health conditions, and patient attitudes or disposition, as follows: Event type values can include: Adverse Drug Reaction, Incorrect Directions, Incorrect Drug, Incorrect Package to Patient, Incorrect Prescriber, Incorrect Quantity, Incorrect Strength, Mixed Incorrectly, and Other. Patient's Alleged Health Condition values can include: Adverse Rx Reported, Deceased, Hospitalized, No Adverse Rx Reported, Required MD Office Visit, and Unknown. Patient's Alleged Attitude values can include: Concerned, Extremely Upset, Not Concerned, Unknown, and Very Concerned. The user can select to "continue" onto the next interface screen, which is the "event recap" interface screen shown in FIG. 7, go "back" to the "Enter Script #" interface screen shown in FIG. 5, save the data entered to the error event database 210, 310, 410, 510 by clicking on the "Save As Draft" button, or cancel the screen by clicking on the "Cancel" button. If the "Save As Draft" button is selected, the user can then choose the other buttons to continue to the next interface screen, go back to the previous interface screen, or cancel out of the error event capture screens altogether. If the "Save As Draft" button is selected, the entered data is also associated with or saved within the external event table 1900 of the relational database shown in FIG. 4 and/or other error events tables in the database.

Figure 7:
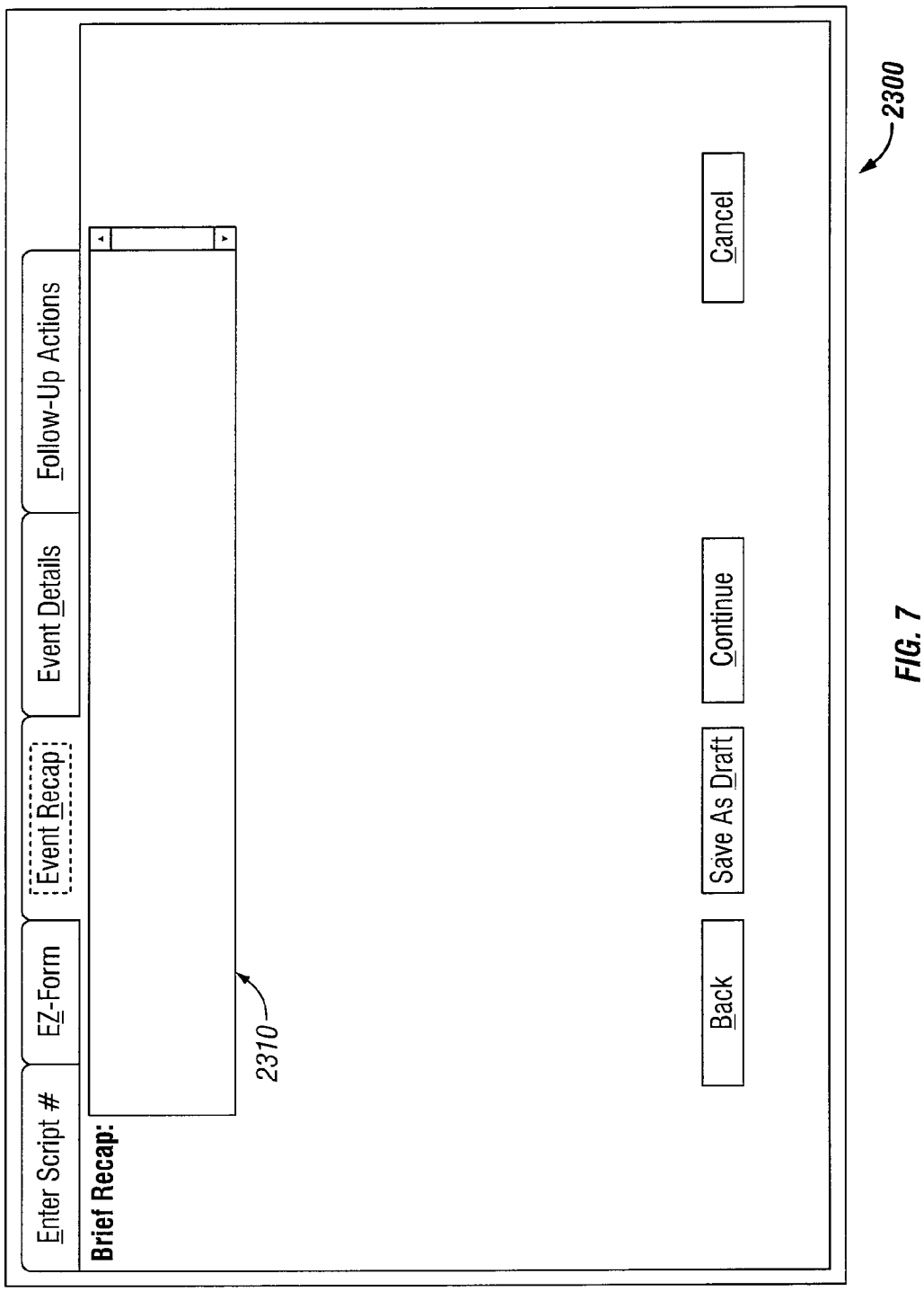
FIG. 7 is a further interface screen of one embodiment of the system of FIG. 1 providing for entry of some additional error event data and analysis information.

Referring additionally to FIG. 7, a further error event capture interface screen, entitled "Event Recap" interface screen 2300 is shown. A brief recap field 2310 is provided for allowing the user (pharmacist or technician) to enter a brief description of the pharmacy error event. In one embodiment, the brief recap field 2310 allows for 1500 characters to be entered. The user can select to "continue" on to the next interface screen, which is the "event details" interface screen shown in FIG. 8, go "back" to the "EZ Form" interface screen shown in FIG. 6, save the data entered to the error event database 210, 310, 410, 510 by clicking on the "Save As Draft" button, or cancel the screen by clicking on the "Cancel" button. If the "Save As Draft" button is selected, the user can then choose the other buttons to continue to the next interface screen, go back to the previous interface screen, or cancel out of the error event capture screens altogether. If the "Save As Draft" button is selected, the entered data is also saved within or associated with the external event table 1900 of the relational database shown in FIG. 4 and/or other error events tables in the database. Similar to the other error event data capture interface screens, if a brief recap has previously been entered for an error event, then this previously entered data will appear in the brief recap field 2310, which can then be modified and saved.

Figure 8:
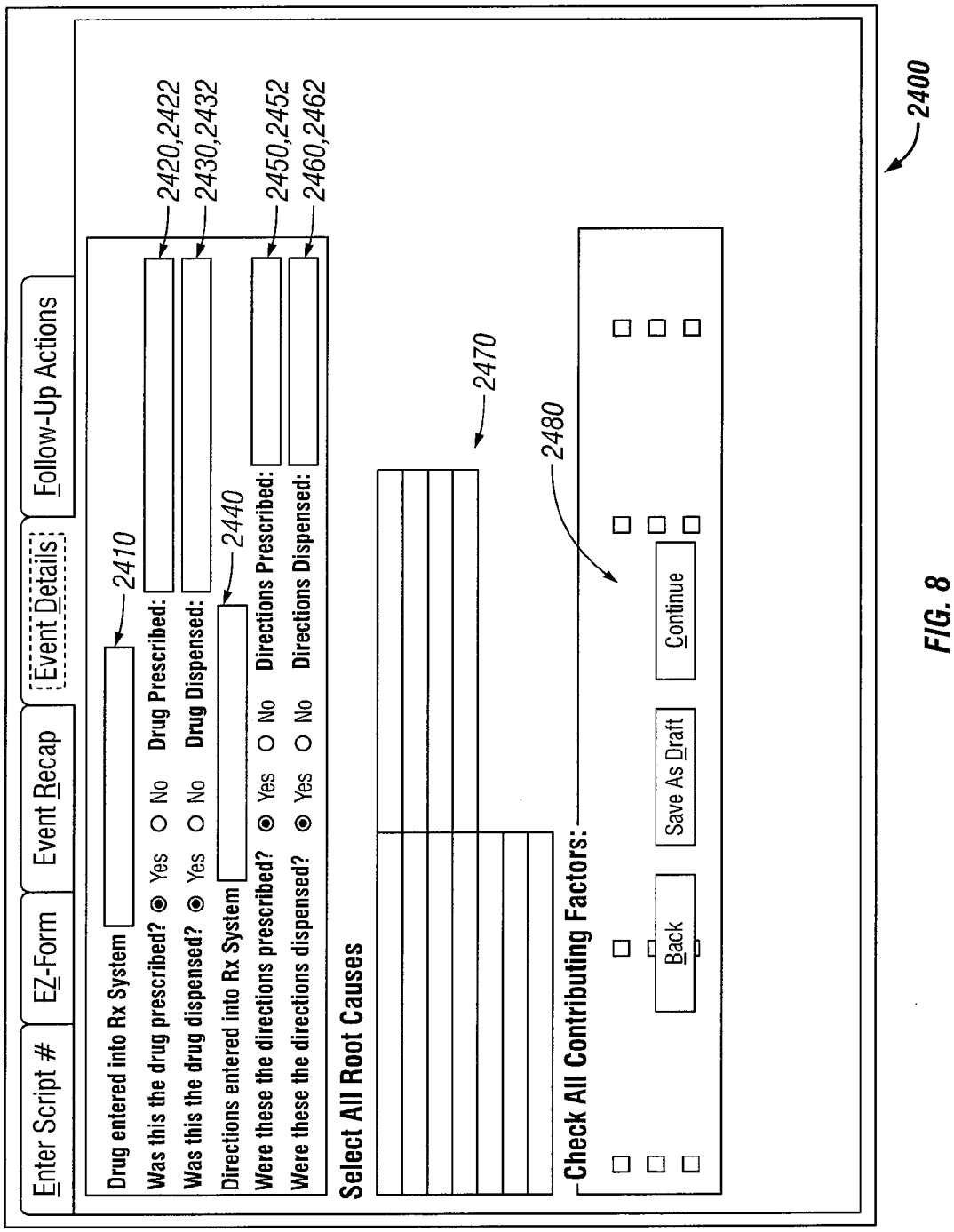
FIG. 8 is a further interface screen of one embodiment of the system of FIG. 1 providing for entry of some additional pharmacy error event data and analysis information.

Referring additionally to FIG. 8, a further error event capture interface screen, entitled "Event Details" interface screen 2400 is shown. This interface screen is provided for entering details regarding the pharmacy error event. In one embodiment, a user does not have access to this screen "tab" unless they have selected an event type in the EZ Form interface screen 2200 of FIG. 6. The user can enter various detailed error event data into the fields provided by the interface screen, which include a drug entered into the prescription system field 2410. The drug entered into prescription system field 2410 is automatically populated with the product name (in abbreviated format), which is returned from the database 210, 310, 410, 510 having prescription information therein. A "was this drug prescribed" check box 2420 and drug prescribed field 2422 are provided. If yes is chosen, then the field "drug prescribed" 2422 is prevented from use. However, if no is selected, then the drug actually prescribed is entered into the "drug prescribed" field 2422 (or selected from a pre-populated set of data). A selection of "no" indicates that the drug entered into the prescription system was not the drug prescribed. A "was this the drug dispensed" check box 2430 and drug dispensed field 2432 are provided. If yes is chosen, then the field "drug dispensed" 2432 is prevented from use. However, if no is selected, then the drug actually dispensed is entered into the "drug dispensed" field 2432 (or selected from a pre-populated set of data). A selection of "no" indicates that the drug entered into the prescription system was not the drug dispensed. A "directions entered into prescription system" field 2440 is provided and can be automatically populated from the database 210, 310, 410, 510. A "were these the directions prescribed" check box 2450 and directions prescribed field 2452 are provided. If yes is chosen, then the field "directions prescribed" 2452 is prevented from use. However, if no is selected, then the directions actually prescribed are entered into the "directions prescribed" field 2452 (or selected from a pre-populated set of data). A selection of "no" indicates that the directions entered into the prescription system were not the directions prescribed. A "were these the directions dispensed" check box 2460 and directions dispensed field 2462 are provided. If yes is chosen, then the field "directions dispensed" 2462 is prevented from use. However, if no is selected, then the directions actually dispensed are entered into the "directions dispensed" field 2462 (or selected from a pre-populated set of data). A selection of "no" indicates that the directions entered into the prescription system were not the directions dispensed.

"Select all root causes" fields 2470 request the user to select all reasons for the event type entered into the event type field 2215. The event type value is passed to the event details interface screen 2400 and displayed in the text about the "select all root causes" fields or buttons 2470. These buttons are populated by the reasons associated with the event type, from the database 210, 310, 410, 510. When user hovers over a reason (button), it will be highlighted. The user will select a reason or sub-reason by clicking on the button. A button can be de-selected. A sub-reason can be provided as well. The user can select as many reasons or sub-reasons as they want and as apply. If a reason has sub-reasons within it, the user will be prompted to select sub-reason(s) by an arrow on the reason. The user will know that a reason has been selected because it will stay highlighted. All possibilities for each event type will be displayed for choosing.

"Select all contributing factors" fields 2480 request the user to select all contributing factors for the event type entered into the event type field 2215. The event type value is passed to this interface screen and is displayed in the text about the "select all contributing factors" fields or check off boxes 2480. The root causes 2480 can automatically be populated from the database 210, 310, 410, 510. In one embodiment, possible contributing factors can include: Handwriting, QuickCodes, Training, MultipleRx, Drug, Totes, Updating, ClearBags, Drug Location, Language, Refrigerated, and/or Packaging. The user can select to "continue" on to the next interface screen, which is the "follow-up actions" interface screen shown in FIG. 9, go "back" to the "event recap" interface screen shown in FIG. 7, save the data entered to the error event database 210, 310, 410, 510 by clicking on the "Save As Draft" button, or cancel the screen by clicking on the "Cancel" button. If the "Save As Draft" button is selected, the user can then choose the other buttons to continue to the next interface screen, go back to the previous interface screen, or cancel out of the error event capture screens altogether. If the "Save As Draft" button is selected, the entered data is also saved within or associated with the external event table 1900 of the relational database shown in FIG. 4 and/or other error events tables in the database. Similar to the other error event data capture interface screens, if one or more error event data have previously been entered for an error event, then this previously entered data will appear in the fields, which can then be modified and saved.

Referring additionally to FIG. 9, further details of the capture and investigation activities for an error event are captured through a follow-up actions interface screen 2500. Specifically, a "did the patient return correct medication?" field 2510 is provided for requesting the user to select yes, no or unknown to this requested data. A "did the patient receive correct medication?" field 2520 is provided for requesting the user to select yes, no or unknown to this requested data. A "was the doctor contacted?" field 2530 is provided for requesting the user to select yes, no or unknown to this requested data. If the user selects the yes box for the "was the doctor contacted?" field 2530, the user can enter any comments from the doctor in an "MD comments" field 2540. A "did the patient receive a refund?" field 2550 is provided for requesting the user to select yes, no or unknown to this requested data. A "was insurance notified (per Supervisor)?" field 2560 is provided for requesting the user to select yes, no or unknown to this requested data. If the user selects the yes box for the "was insurance notified" field 2560, the user can enter the insurance claim number in a "claim #" field 2562. An out-window staff initials field 2570 is provided for requesting the user to enter the initials of the personnel which delivered the prescription to the patient at the pharmacy window. The database 210, 310, 410, 510 can store initials to name cross-reference data such that the entering of initials will allow the system to identify such personnel. If the out-window personnel is unknown, an unknown check-off box is provided as a part of the out-window staff initials field 2570.

When the full error event data capture is completed, the user can click on a "Submit" button 2580. In one embodiment, at that time the error event data capture software module(s) 700, 730, 750 of system 100 validates at least the following fields. Specifically, the system validates that an event type has been entered through event type field 2215. If user selects "yes" to the question "was the medication used?", the system validates whether the user has entered data in the "how many doses were used?" field 2225. The system also validates whether data has been entered in the brief recap field 2310. If the user selects the no check-off box for one or more of the "was this the drug that was prescribed?" field 2420, "was this the drug that was dispensed?" field 2430; "were these the directions that were prescribed?" field 2450; and/or "were these the directions that were dispensed?" field 2460, the system further validates whether the user entered data in the respective drug prescribed field 2422, drug dispensed field 2432, directions prescribed field 2452, and/or directions dispensed field 2462. The system also validates whether at least one root cause and/or one contributing factor was selected from the select all root causes fields 2470 and/or the check all contributing factors fields 2480. If a user selects the "yes" check-off box for the was the doctor contacted field 2530, the system validates whether the user entered any data in the MD Comments field 2540. If a user selects the "yes" check-off box for the "was insurance notified?" field 2560, the system validates whether the user entered the claim number in the Claim #field 2562. The system also validates whether any data was entered in the out-window staff initials field 2570 (either initials or "unknown" checked). If the system validation fails for one, some, of all of the above checks, the error event data capture software module(s) 700, 730, 750 can direct the user to go back and enter such information, and directs that the error event record may not yet be "submitted" for review and consideration by supervisory personnel. Other fields mentioned herein may be added to this validation procedure as well. A message window or interface screen can appear to provide exact details on what the user still needs to do or perform for a successful submission of an error event record.

Figure 10:
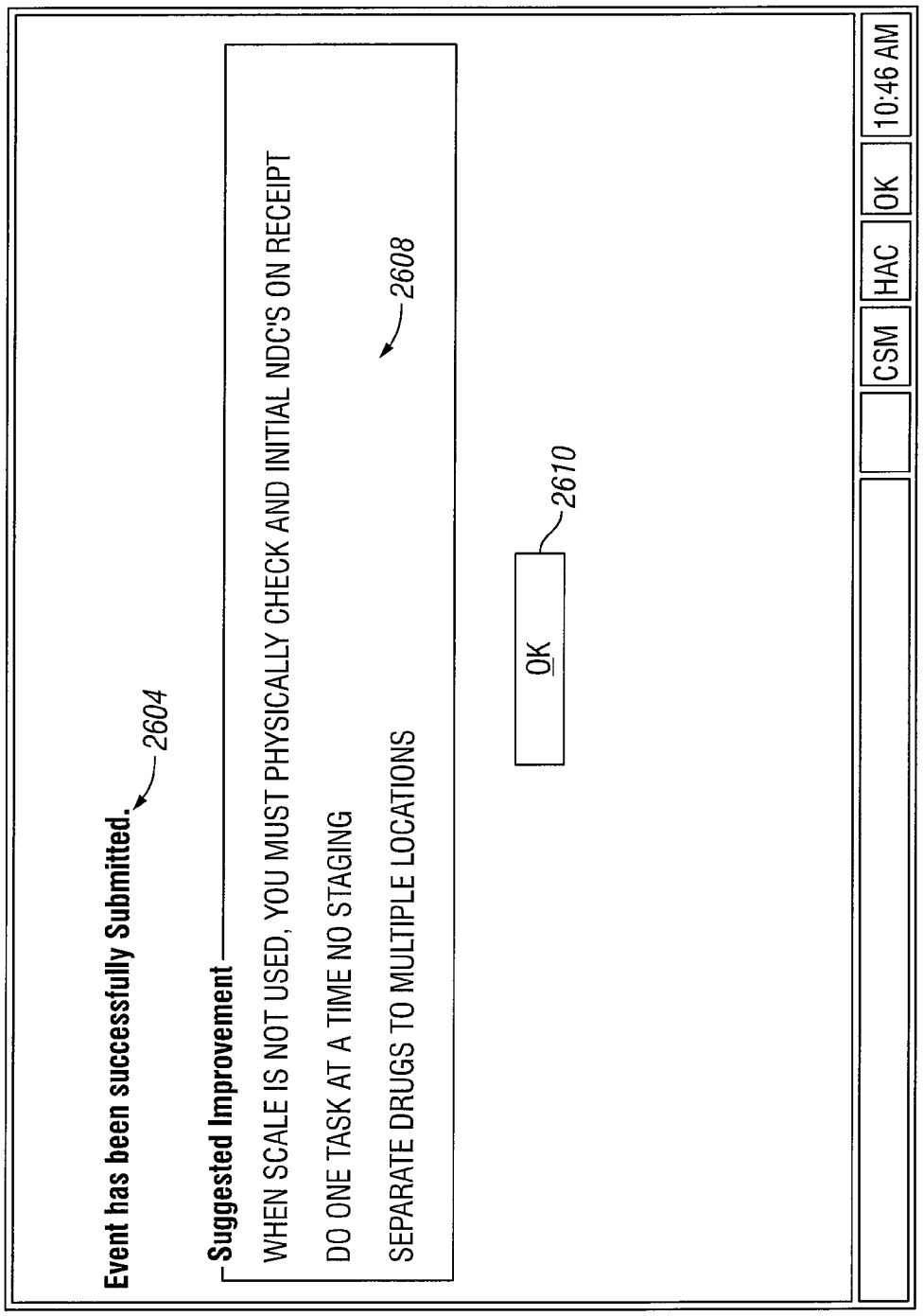
FIG. 10 is a further interface screen of one embodiment of the system of FIG. 1 providing suggested improvements for quality improvement in relation to a pharmacy error event.

Referring additionally to FIG. 10, once all necessary data and information is entered within the error event data capture and investigation interface screens of at least FIGS. 5 through 9, a message window or interface screen 2600 can appear to inform the user that a successful submission 2604 has taken place for the error event record. As shown in FIG. 10, in one embodiment, suggested improvements 2608 can be provided right away to the user in relation to the error event record just submitted in order to continuously attempt to improve the quality of the pharmacy prescription filling function. As shown, at least improvement suggestions of making sure specific checking procedures are followed and other more general suggestions, such as to not perform multiple tasks at the same time and/or using spaces appropriately, can be provided. The message window or interface screen 2600 can also include an "OK" or acknowledgment input 2610 requiring the user to acknowledge that he or she has read the suggested improvements. If the person entering the error event record is not the personnel responsible for the error event or not the person at the out-window for the error event record being submitted, the system may store a record of this information and require that such personnel review the error event record and suggested improvements at a later time, as will be described below. Whether or not the person entering the error event record is the same person, as mentioned, such later error event record review with suggested improvements may still be required. Time limits may be provided in the system for such review to occur, and notification to such personnel can be provided by the system through internal communications mechanism and/or through more traditional means such as by e-mail. The system can be interfaced to pharmacy and/or enterprise e-mail systems for automated communication of such notifications.

Figure 11:
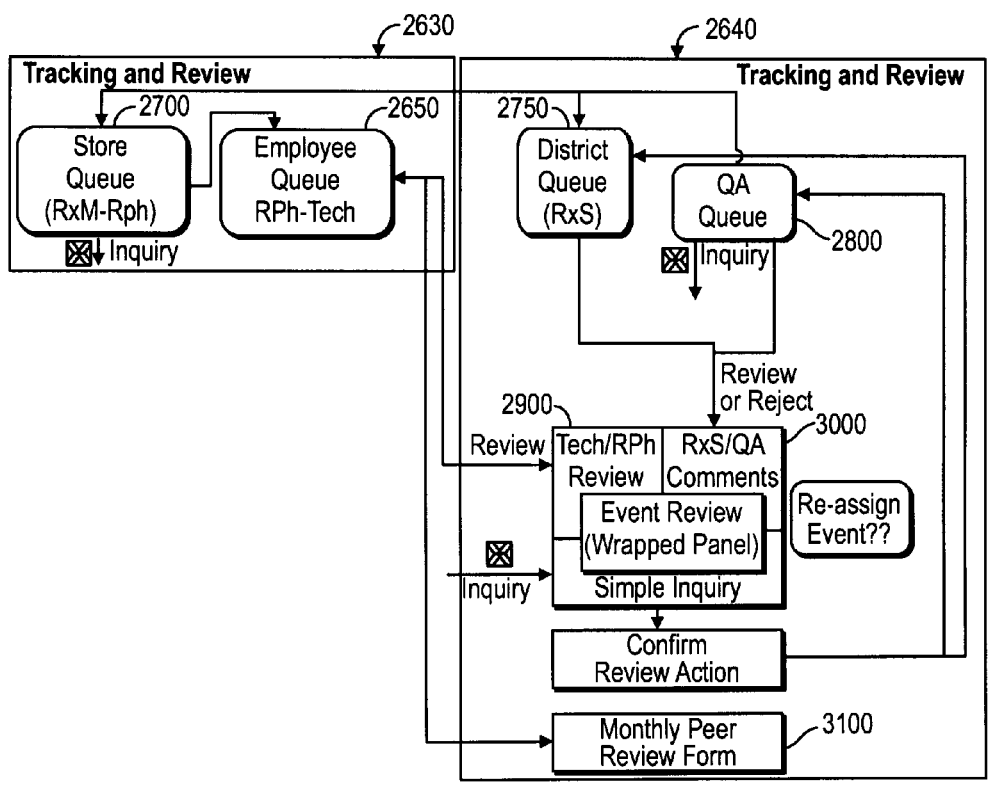
FIG. 11 is an interface functional flow diagram of one embodiment of the system of FIG. 1.

Referring to FIG. 11, depending on the position and level of internal security and access of personnel within the pharmacy and pharmacy enterprise, the system 100 and in particular error event tracking and review modules 900, 910 of FIGS. 2 and 3, these modules can provide access to appropriate interfacing functionality for the various personnel through various interface queues. Specifically, at the store level 2630 technicians and pharmacists are provided access to an employee queue or employee interface screens 2650 and respective functionality. Referring also to FIGS. 12 and 15(*a*) to 15(*f*), the employee queue 2650 enables the pharmacy staff having access to such screens, to review external or other events they are associated with (i.e., they performed any action associated with the fill that caused the event), as indicated through Tech/RPh Review box 2900 of the Event Review module shown in FIG. 11. Thus, once error event records are submitted through the capture interface screens, pharmacists and technicians can review error events they were associated with through the employee queue 2650, which may also involve reviewing suggested improvements, and acknowledging such suggested improvements were reviewed. The employee queue 2650 also shows all external and other events for a predetermined time period, such as the past 12 months, sorted by whether they have been reviewed, then by capture date. The following table shows the actors which use each queue and one main purpose for each such queue:

| | QUEUE: | | | |
|---|---|---|---|---|
| | Store Queue | Employee Queue | District Queue | QA Queue |
| ACTORS: | RxM RxPh SM | Technicians RxM RxPh | RxS DM | QA |
| | Manages events that need to be handled in the store | For pharmacy staff to review events they were associated with | To review store events and ensure they have been handled appropriately | To double check that events have been handled appropriately, then file them |

Figure 20:
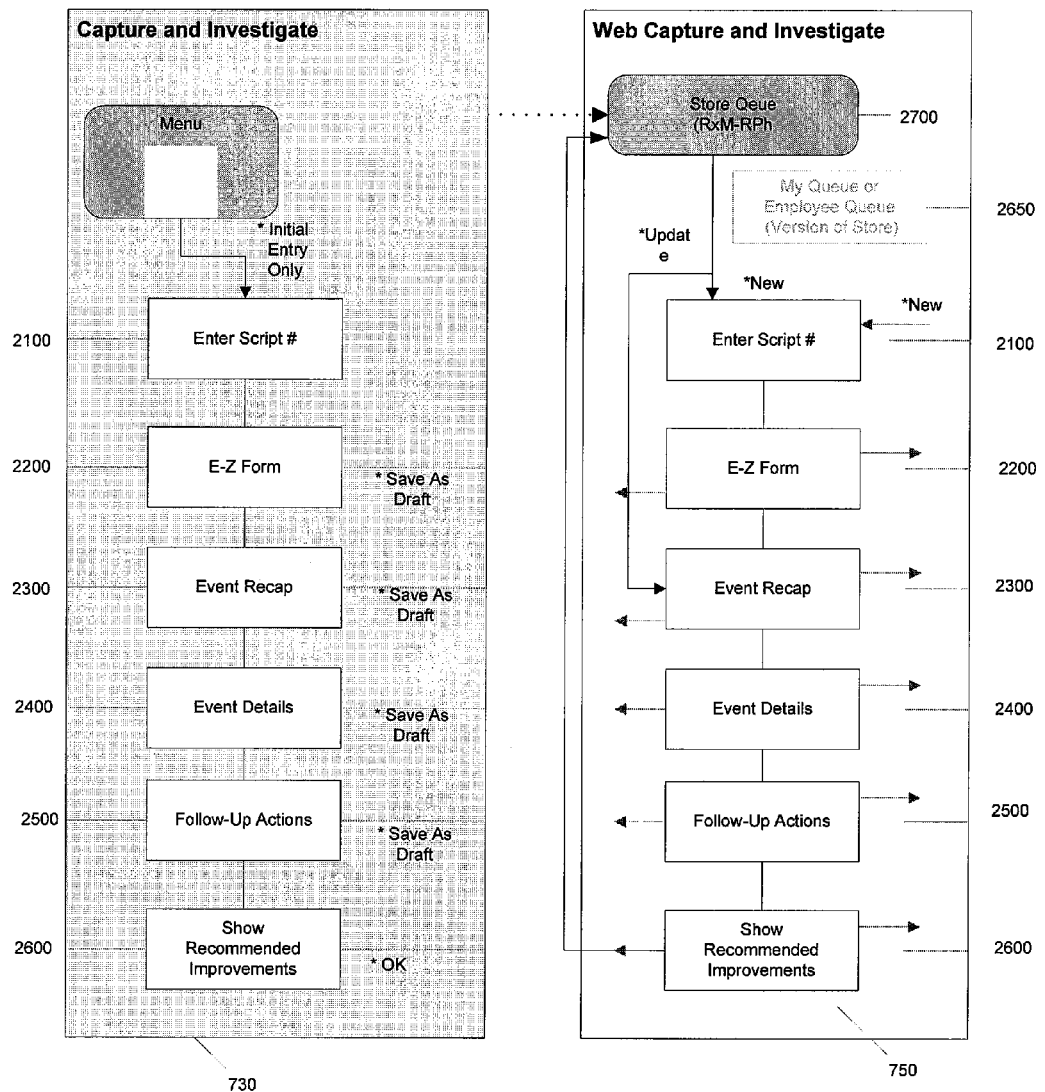
FIG. 20 is a functional flow diagram of functional modules of one embodiment of the system of FIG. 1.

Also at the store level 2630, staff pharmacists and pharmacy managers are provided access to a store queue or store interface screens 2700 and respective functionality. The store queue 2700 enables the pharmacy staff having access to such screens to manage external events. The store queue 2700 also shows all external and other events for a predetermined time period, such as the past 12 months, sorted by priority of action, and highlighted for any error events requiring immediate attention. Referring briefly to FIG. 20, in one embodiment, the store queue 2700 can provide access to error event data which is captured through capture and investigate interface screens 730, 2100, 2200, 2300, 2400, 2500, 2600, which are located at and/or launched from a local pharmacy computer 200, 300, 400, which can be a non-web-based application and interface. In this embodiment, the store queue 2700 can also allow a user to capture and investigate error events through web-based capture and investigate interface screens 750, 2100, 2200, 2300, 2400, 2500, 2600. The user can move from one web-based capture and investigate interface screen 750 to another without having to follow a particular flow of screens, or top to bottom flow can be required. Also, the user can move to other non-capture and investigate screens, as are being described.

Referring also to FIG. 14, at a district and/or corporate/quality assurance level 2640, pharmacy supervisors such as a district managers are provided access to a district queue or district interface screens 2750 and respective functionality. The district queue 2750 enables the supervisor staff having access to such screens, such as RxS's and/or district managers, to review, forward and/or reject external and other error events, as indicated in FIG. 11. The district queue 2750 shows external and other error events from the last rolling predetermined time period, such as 12 months, for the RxS and/or district manager at the district level 2640. Results can be filtered or sorted by any column, and the user can drill down on any error event for review and/or decision making by clicking an associated hyperlink.

Figure 13:
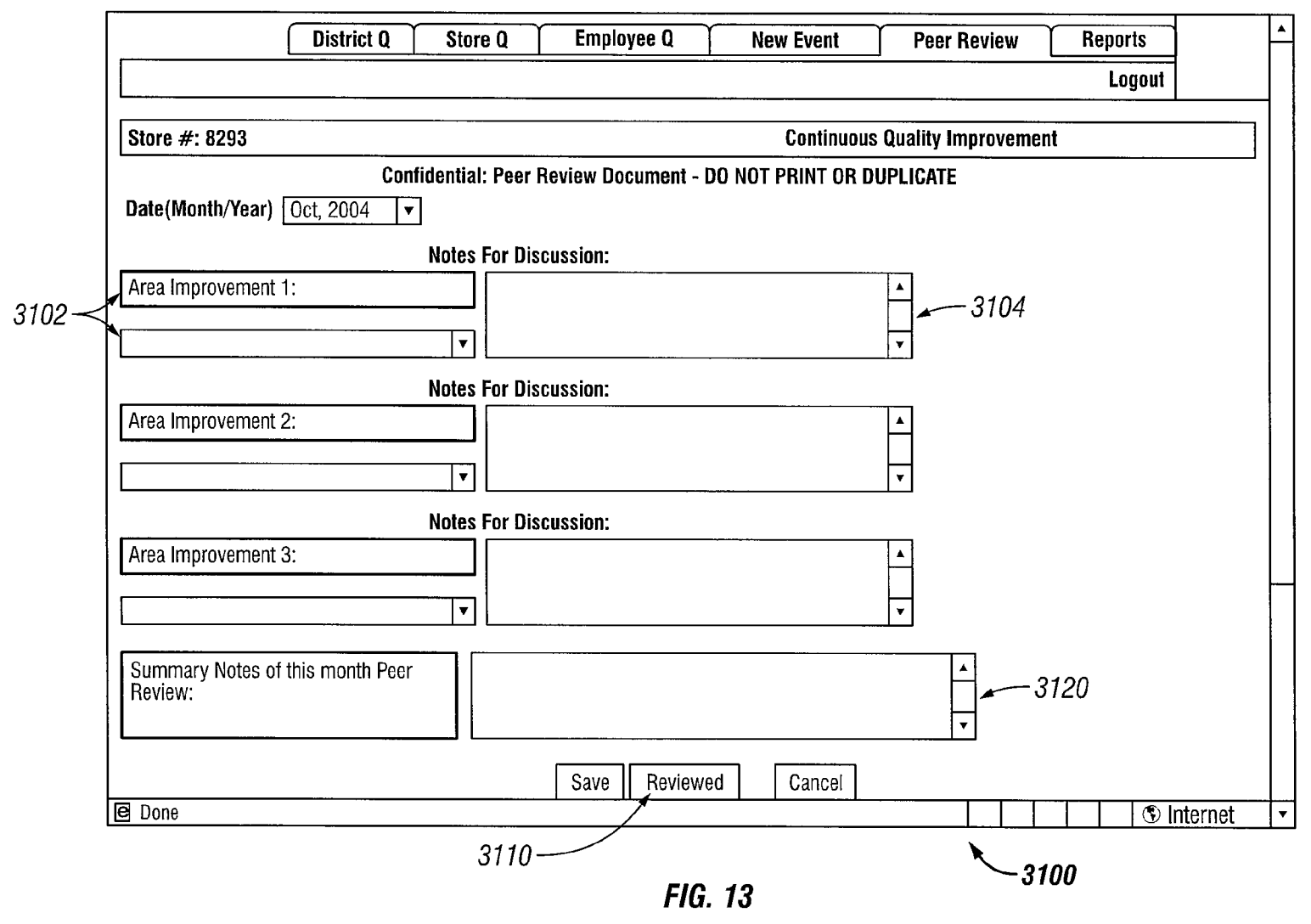

At the district and/or corporate/quality assurance level 2640, corporate and/or quality assurance personnel are provided access to a quality assurance (QA) queue or quality assurance interface screens 2800 and respective functionality. The QA queue 2800 enables a QA analyst or other corporate supervisory staff having access to such screens, such as RxS's, to review, forward and/or reject external and other error events. The QA queue 2800 shows external and other error events from the last rolling predetermined time period, such as 12 months, for the RxS at the quality assurance level 2640. Results can be filtered or sorted by any column, and the user can drill down on any error event for review and/or decision making by clicking an associated hyperlink. The district and QA supervisory personnel can evaluate the investigation, findings and follow-up actions being performed by the store pharmacist and/or technician for an error event record, and the district and QA supervisory personnel can provide comments within the system 100, through an RxS/QA Comments module 3000 shown in FIG. 11. Lastly, pharmacy managers can record continuous quality improvement peer review meeting notes within a Monthly Peer Review Form module 3100, which pharmacy staff can review and acknowledge, and in one embodiment must review and acknowledge through the employee queue and/or store queues 2650, 2700. As shown in FIG. 13, a peer review interface screen 3100 enables the RxM to document the minutes from the Monthly Peer Review, including tracking agreed upon focus points—those suggested improvements where the pharmacy and or individual is placing particular emphasis. As mentioned, the peer review interface screen and module 3100 is used by the pharmacy staff to review the minutes and electronically sign off that the staff have read such minutes.

A read-only error event interface screen can also be provided through the system software for displaying the details of an error event, such as an external error event. The information displayed is generally the same as shown and described in the error event capture interface screens, except the information is presented as a read-only scrolling list of information. This interface screens and information can be used by (1) RxS and QA analysts to review an error event, (2) pharmacy staff to review their participation in external events, and (3) all personnel when they are just inquiring against an event to see the event details.

The district queue 2750 provides pharmacy supervisors and district managers with a view of error events which the stores (pharmacies) in their district have submitted, resubmitted or not completed within a predetermined time frame, such as in 72 hours. The district queue 2750 allows this personnel to review, forward to QA, or reject with comments, or return the event to the store, as indicated in at least FIGS. 11 and 19. The system allows QA a view of all events which have been reviewed and forwarded by pharmacy supervisors, or have not been completed by the store in a predetermined time frame, such as 14 days.

Referring again to FIG. 12, when a technician and/or pharmacist logs into the system as a user, the user will see three sets of interface screens to chose from: 1) the employee queue 2650; 2) a peer review interface 2652 similar to that shown in FIG. 13, only with information filled in the area of improvement box 3102 and/or the notes for discussion 3104, and the option to choose "Reviewed" 3110 available to select; and 3) a reports interface screen 2654. Only data and information from the database 210, 310, 410, 510 associated with the login ID for the user logged in will appear in the employee queue 2650, peer review interface 2652, and reports interface 2654. In particular, only error event data and information which the particular user opened, modified, and/or submitted as an error event record will be available. Additionally, or alternatively, error event data and information for records which of error events which the user was directly involved will appear for review and/or action. In one embodiment, only these interface screens will be available to a technician employee. This screen shows a list of all events associated with an employee that were captured in a predetermined time frame, such as the last 12 months. A sub-panel (peer review interface 2652) shows the results of the latest peer review meeting. The employee queue 2750 interface screen can show also show all events the employee is involved in, regardless of the store for an employee who works at multiple stores within a pharmacy enterprise. Users of this interface screen can include employees who need to review which events they are involved in (accessible by employee login), and pharmacy supervisors for reviewing what events an employee has been involved in (available by following a link from an event review interface screen or panel from the track and review module 910).

Referring again to FIG. 13, several additional interface screens are available to a user with a higher level of access for the system, such as the district queue 2750, store queue 2700, etc. As mentioned, the peer review interface screen 3100 shows how an employee or supervisor can enter information about suggested improvements, on a per store basis. The area improvements 3102 can be selected from a pre-populated list by supervisory personnel. The pre-populated list can be determined by the pharmacy error event software 220, 320, 420, 520 by choosing only those area improvements which apply to a particular error event record based on error event type, root causes and/or sub-root causes, contributing factors for one or more error events by individual, store, district, or other combinatorial factor or criteria. A space for notes 3104 is provided as well, for each area of improvement. A summary space 3120 is also provided. The system will track whether a review occurred and who performed the review. If pharmacy staff, such as a technician, clicks on the "Reviewed" button 3110, the system will take the user back to the employee queue interface screen 2560. The value under the "Reviewed" heading in the employee queue 2650, will be changed to "Yes" for this error event record (shown by Error No.).

Referring additionally to FIG. 14, the district queue interface screen 2750 is shown. Access to this interface screen 2750 is only provided to pharmacy or pharmacy enterprise personnel having an appropriate supervisory level login. The error event data shown in this interface screen can be listed and searched by event, store, date range, patient name, event type, patient condition, patient attitude, status of record (QA Rejected, Draft (if overdue), Submitted to RxS, RxS Draft, RxS Rejected, Submitted to QA, QA Draft, QA Filed), and/or other "filter" criteria. Additional error event data such as dose taken, patient attitude, status of an event record can be displayed to the user, as shown. Specific rules for which event should automatically display as a part of the district queue 2750 are a part of the error event software 220, 320, 420, 520, as well as rules for which error event records should automatically be highlighted. A user having a high enough log-in level can change these rules. In the example interface shown in FIG. 14, the first four error event records are highlighted, which indicate all error event records which are in "draft"

form at the store level, which indicate that such records have not been completed by the store, and have not yet been submitted to the RxS. Error event records can also be highlighted when an error event record is overdue from the Store to the RxS, or overdue to the QA analyst from the RxS. The interface screen shows all event records that need to be worked on by the RxS as well, which includes any in the following statuses: "submitted to RxS" (shown), and "RxS Draft" (not shown). In one embodiment, the RxS cannot see error event records that are still in "Save As Draft" form within the store until after a predetermined period of time passes since the record was opened, such as after 72 hours have elapsed. This and other predetermined time periods within this specification can be changed by a user having a high enough log-in level. At least the displayed error event record number ("Event#) can be "clicked" on which, through an html hypertext link, will take the user to details of the error event data for at least QA review functions, such as those provided through employee queue interface screens in FIGS. 15(a) through 15(f). These interface screens shown in FIGS. 15(a) through 15(f) can be used by the RxS and DM to review error events and ensure such error events have been handled appropriately. As will be explained in greater detail below, error events can be escalated by communicating an email to the RxS when the error event is overdue and in a status of draft or "RxS Rejected." (See FIGS. 16 and 19).

Referring additionally to FIG. 15(a), an employee queue interface screen 3200 for an individual error event record is shown. This screen contains two parts. The first part is an event review panel 3210 that is scrollable and displays all the details of the event under review. Various data and information is shown in FIGS. 15(a) through 15(f). In addition, a "Reviewed" box 3212 is provided for the user, such as a district manager, to input into the system that the user has reviewed the error event record, and that such error event record is now ready for review by higher supervisory level personnel, such QA personnel. Personnel review information 3214 listing what personnel is involved with (which person performed patient entry, performed prescription entry, performed filling tasks, performed up-front verification, performed product review tasks, as well as performed out window delivery tasks). The software and database track this personnel review information 3214, and also track whether personnel involved with the error event record have reviewed the error event record, as shown in FIG. 15(d). The second part of this interface screen is a reviewer panel 3220 located toward the bottom of the screen, which operates in one of two modes. Specifically, in manager review mode, when an RxS (district supervisor) or QA analyst is reviewing an error event, this user can reject 3222, submit 3224, or Save As Draft 3226. In staff employee review mode, the staff employee in the pharmacy can review an error event and electronically sign off on the error event. There is also a simple inquiry mode wherein the user can view the error event without being able to take any specific further actions. In at least one of the review modes, the user can indicate whether a settlement has been made with the patient, whom the settlement check should be made out to (or was made out to), and an indication of where the check should be sent or was sent. The reviewer panel 3220 located toward the bottom of the screens in FIGS. 15(a) and 15(f) are used by an RxS to review the event, submit to QA or reject the event. This panel can also be used to record an insurance settlement and extend the deadline 3228 if the error event record is beyond the predetermined time frame for taking action such as submitting an error event record for review to the RxS or QA. As mentioned, a review panel is used by an technician and/or pharmacist in the pharmacy to review an error event record they were involved in. The "Reviewed" button 3212 appears at the bottom of the scrolled event review panel to ensure that the employee reviews the complete event.

The error event records are reviewed by employees, supervisors, and others, and determinations are made as to whether a settlement is needed with patients. This information is tracked, and if the error event record is not reviewed and concluded (by some resolution such as settlement) within certain time frames, as tracked by the system, the events are escalated. Escalation can occur in many ways, such as by automatic notification of supervisors, district managers, etc. Referring additionally to FIG. 16, a table is shown which shows valid destinations from each queue and the allowable sub-actions. When an error event record is selected from a queue, the destination is either the Event Review interface screen in the track and review module 910 or New Event to Event Recap (Capture) interface screens in the web capture and investigate module 750. The Event Review interface screens can operate in one of several modes: RxS/QA review mode (Rvw), RxS/QA extend mode (Xtnd), Employee Review mode (Rvw) or Inquiry mode (Inq). The destination and mode combinations are based on the role of the user (i.e. who is logged on), the status of the event, and the queue they are operating from. FIG. 16 details the results. For example, if the error event record is "owned" by the store and the "status" is Store Draft, and the user is coming from the Store Queue, then New Event-Capture-Event Recap is the destination. Likewise, if coming from the District Queue and if overdue to the RxS (over 72 hours old in one embodiment), then Extend mode is the destination. The default drop-through action is Event Review—Inquiry or Review mode (no highlights), with review mode if the user was involved in this event and has not yet reviewed it.

Figure 19:
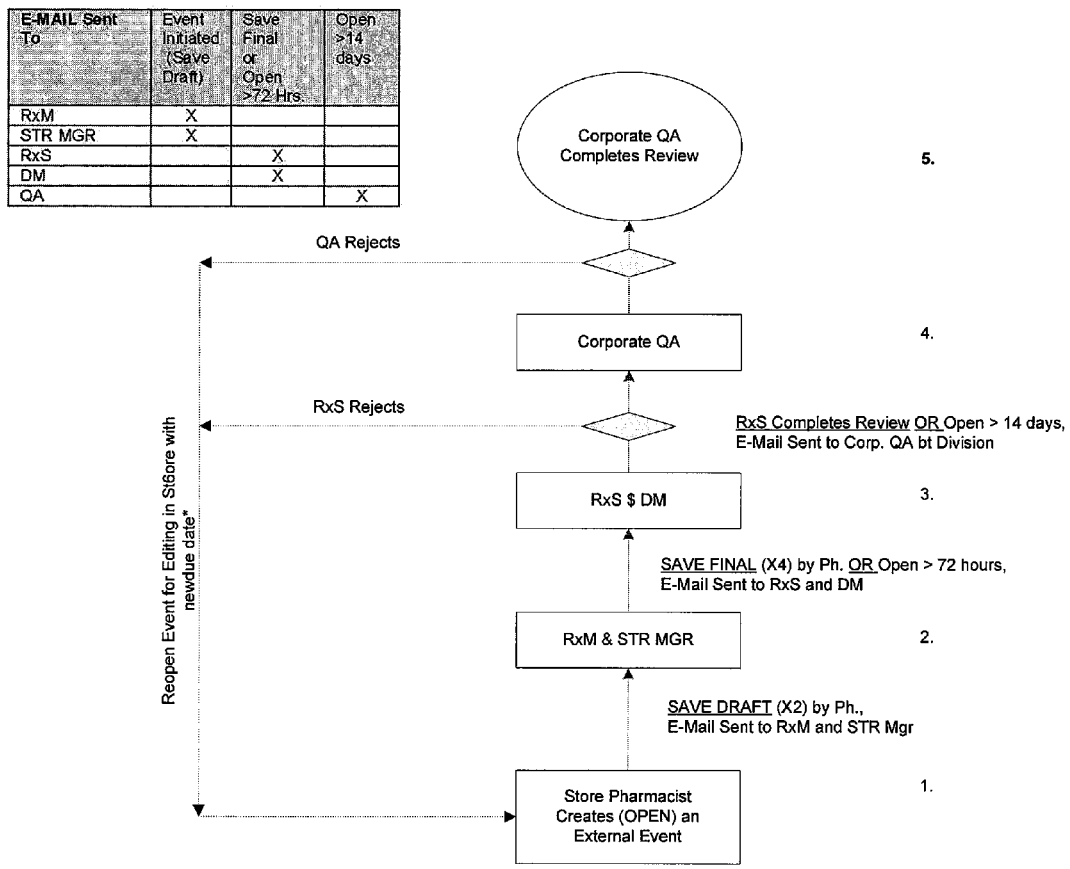
FIG. 19 is a flowchart and table of one pharmacy error event tracking method of the system of FIG. 1.

One embodiment of escalation is shown in FIG. 19. Specifically, the error event tracking and review module 910 is used by the Pharmacy Supervisor (RxS) and QA to review at least external events submitted in pharmacies. Once an error event record is opened or initiated, a pharmacist can save it as a draft as many times as they like. A communication such as an e-mail is sent to both the RxM and store manager upon the opening of an error event record. In one embodiment, the pharmacist must complete investigation within 72 hours after an external event is initiated and submit the error event record. If the 72 hours passes or when the investigation is completed by a pharmacist, the Pharmacy Supervisor and District Manager are notified by a communication such as an e-mail. The Pharmacy Supervisor reviews the error event record. They can then forward it to QA or reject it with comments and return it to the store. If the submitted or escalated error event is rejected, the error event is reopened for editing by the store. If a predetermined time, such as 14 days, have passed since the error event record was opened, or once Pharmacy Supervisor completes the review, a communication such as an e-mail is sent to QA for review. QA can file it, or reject it with comments, and return it to the Pharmacy Supervisor RxS. The pharmacy supervisor can then return it to the store further investigation.

Figure 18:
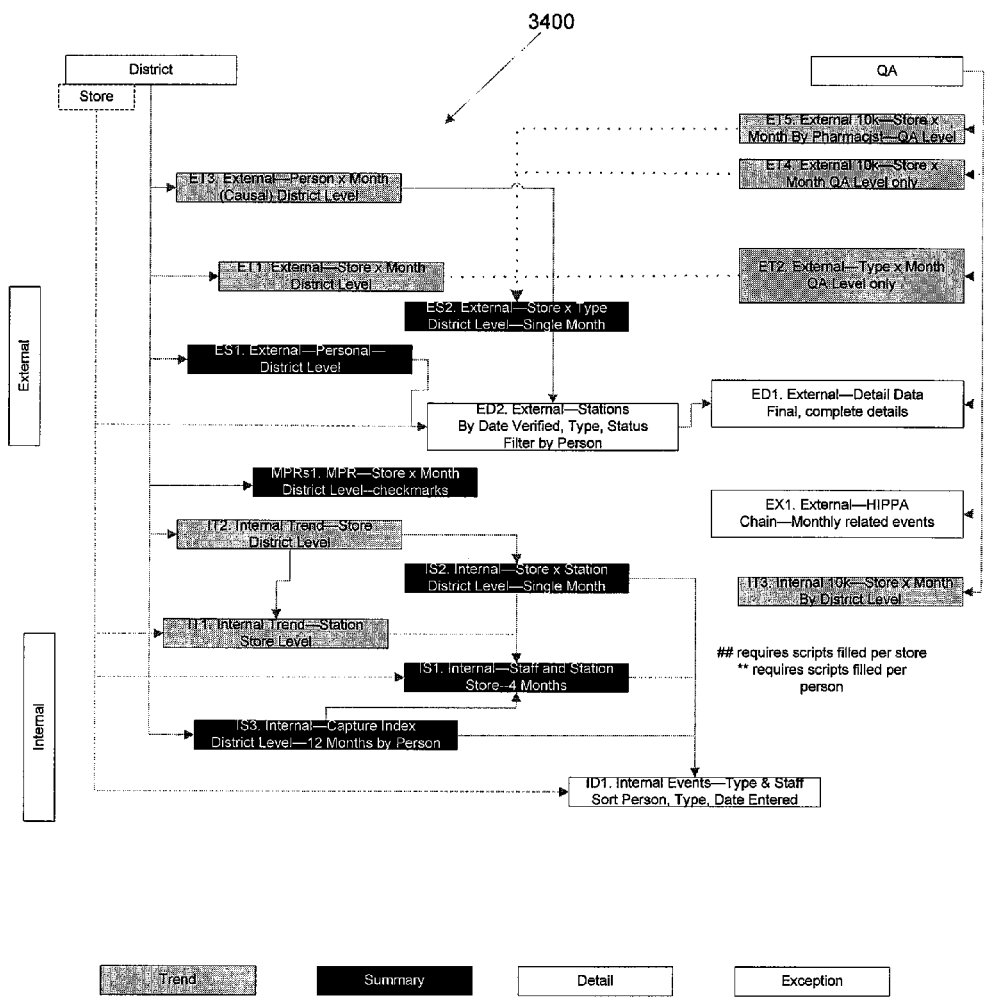
FIG. 18 is a flow diagram of internal and external error event information and functions, including trending information, available at different levels within one embodiment of a pharmacy operation of the system of FIG. 1.

Referring additionally to FIGS. 17 and 18, a reports interface screen 3300 and a report flow diagram 3400 are shown. The error event reporting module 800 tabulate and/or compile error event record data stored in the error event database 210, 310, 410, 510 for trending, external reporting, and other purposes. The below table provides a naming convention to type of report cross-reference, and provides a generally listing of how each report can be sorted and filtered. These reports are described in greater detail after the following table.

| Naming | Report Report Menu | Scope, Sorts and Filters |
|---|---|---|
| | External | |
| ED1. | Detail Data | |
| ED2. | Stations | By Date Verified, Type, Status; |
| ES1. | Person | District Level |
| ES2. | Store x Type | District Level-Single Month |
| ET1. | Store x Month | District Level |
| ET2. | Type x Month | QA Level Only |
| ET3. | Person x Month | (Causal) District Level |
| EX1. | HIPAA Exceptions | Chain wide, by District and Store |
| MPRs1 | Store x Month | District Level-checkmarks |
| | Internal Events | |
| ID1. | Type & Staff | Sort: Person, Type, Date Entered |
| IS1. | Staff x Stations | Store-Single Month |
| IS2. | Store x Stations | District Level-Single Month |
| IS3. | Capture Indexes | District Level-Single Month by Pharmacist |
| IT1. | Station x Month | Store Level |
| IT2. | Store x Month | District Level |

These reports can be generated in real-time dynamic fashion.

In one embodiment, an external events store details report (ED2) is provided for showing external error events occurring within a store within a fixed time period. The information in this report shows external events by work station at the store. The time frame of the report can be the last rolling 12 months. Sorting can be done by workstation and personnel. Filters can include date range, pharmacy staff initials.

A district external events summary by pharmacist (ES1) can be provided for summarizing events by pharmacist. This report can be used by the pharmacy supervisor (RxS) to highlight potential focus points. This report counts external events on a rolling last 12 months basis, and can also list the capture rate of such error events. This report can be sorted by pharmacy staff from the highest to the lowest, based on significant 12 months totals, and by column headers. This report can be linked to external event detail report (ED2), filtered by pharmacist, for related viewing and reporting, as shown in FIG. 18.

A district external events summary by store and type (ES2) can be provided for summarizing events cross-tabled with store and external event type for the pharmacy supervisor (RxS). This report can include external events by type for the previous month (default), and can sort by total events in descending order (highest first). Filters can include date range, and this report can be linked to the ED2 report for a corresponding store.

A district external events monthly by store with last rolling 12 months report (ET1) can be provided for summarizing events by type and store. This report can include external events by store for the last rolling 12 months, and can sort by total error events in descending, highest first order. This report can be linked by month to the ES2 report for a corresponding month, and by cell to the ED2 report (external error event summary) for a corresponding store and month, for related viewing and reporting, as shown in FIG. 18.

A district external events monthly summary by type (ES2) can be provided for summarizing events by type and district for QA review of a district. This report summarizes external events by type on a rolling last 12 months basis. This report can be sorted from highest to lowest, and can be accessed by QA personnel only.

A district external events monthly summary by pharmacist (ET3) can be provided for summarizing events by pharmacy staff across the district. This report summarizes external events by pharmacy staff on a rolling last 12 months basis. The report can be sorted by pharmacy staff from the highest to the lowest, based on the last 12 months totals. This report can be linked to the district external events summary by pharmacist report (ES1) for related viewing and reporting, as shown in FIG. 18.

A summary of HIPAA-related external events (EX1) can be provided for summarizing events that have triggered a HIPAA violation. This report contains external events and patient information, and can be sorted by district and store. The report provides the HIPAA office with a cross-check to ensure that reports are being filed by the stores, but is not the HIPAA filing itself.

A district monthly peer review summary by store and month (MPRs1) can be provided for summarizing MPR/CQI filings by type and store. This report summarizes MPR filings by store and can be sorted by ascending count, starting with the lowest (i.e., worst first). This report can be linked to a specific store's most recent detailed MPR screen.

An internal events detail report (ID1) showing drug name and employee can be provided for summarizing events by type and store. This report summarizes internal events that were caught by pharmacy staff. The report can be sorted by each column, for example by person, type, and date entered.

An internal events summary by employee and workstation (IS1) can be provided for summarizing events by internal event type and store. This report summarizes internal events for the last complete month. The report can be sorted by most total events by person from highest to lowest. This report can be linked to the corresponding ID1 report, for related viewing and reporting, as shown in FIG. 18.

A district internal events summary by store and workstation (IS2) can be provided for summarizing events by type and store. This report summarizes internal events by workstation for a single month, and can be sorted by store within the district. This report can be linked by store to the corresponding IS1 summary by person and station.

A district internal event capture index report (IS3) can be provided for evaluating effectiveness at preventing internal events from escaping the pharmacy. This report contains internal events on a rolling last 12 months basis. This report can be sorted by capture index from lowest to highest. This report can be filtered to only include pharmacists (no technicians) or to only include pharmacists that have external events.

A store internal events monthly by workstation report (IT1) can be provided for summarizing events by workstation and store. This report counts internal events on a rolling last 12 months basis. The report can be sorted by a fixed workstation list. Both the store manager and RxM can view this report, but technicians cannot. This report can be linked to the corresponding IS1 report for the corresponding month and workstation, for related viewing and reporting, as shown in FIG. 18.

A district internal events monthly by store report (IT2) can be provided for summarizing events by type and store. This report counts internal events on a rolling last 12 months basis. This report can be linked to the corresponding IS1 report for the corresponding store and month. This report can also be linked by store number to the corresponding IT1 report to show trends by store and workstation, for related viewing and reporting, as shown in FIG. 18.

An external events monthly prescription error per 10K (10,000 prescriptions) by store report (ET4) can be provided for summarizing events by type and store. This report summarizes external events by type and store and requires summary data of the number of prescription fills per store per month.

A store external events monthly prescription errors per 10K (10,000 prescriptions) by pharmacist report (ET5) can be provided for summarizing events by type and store. This report contains external events by pharmacist.

As indicated and described above, one or more of the above reports and/or data and information contained therein can be electronically communicated to external systems, such as a State Board system 1200, insurance carrier, or other external system 1100. The communication of the information provided in these reports, as explained above, and in other formats, can be automatically electronically communicated to such external systems 1100, 1200 and/or only after a user (corporate personnel) takes some action within the system 100 to cause the information to be sent.

Figure 21:
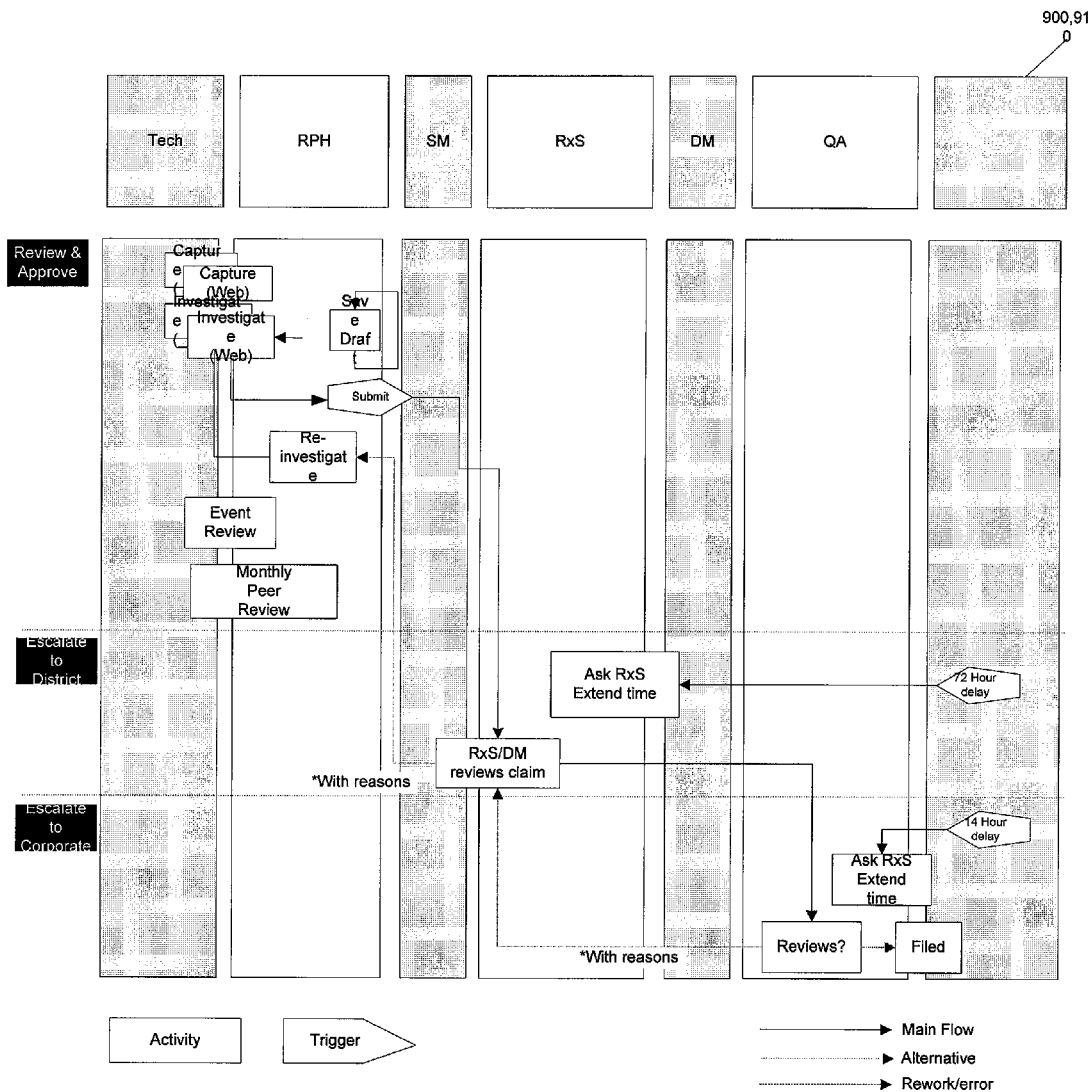
FIG. 21 is a functional flow diagram of the involvement of the personnel with one embodiment of the system of FIG. 1.

Referring to FIG. 21, a functional flow diagram shows the various general activities and triggers and the relationship to one another, by an actor using the system 100. The system 100 and pharmacy error event software 220, 320, 420, 520 implement this functionality as explained above, and as understood by reference to the other portions of this specification.

Figure 22:
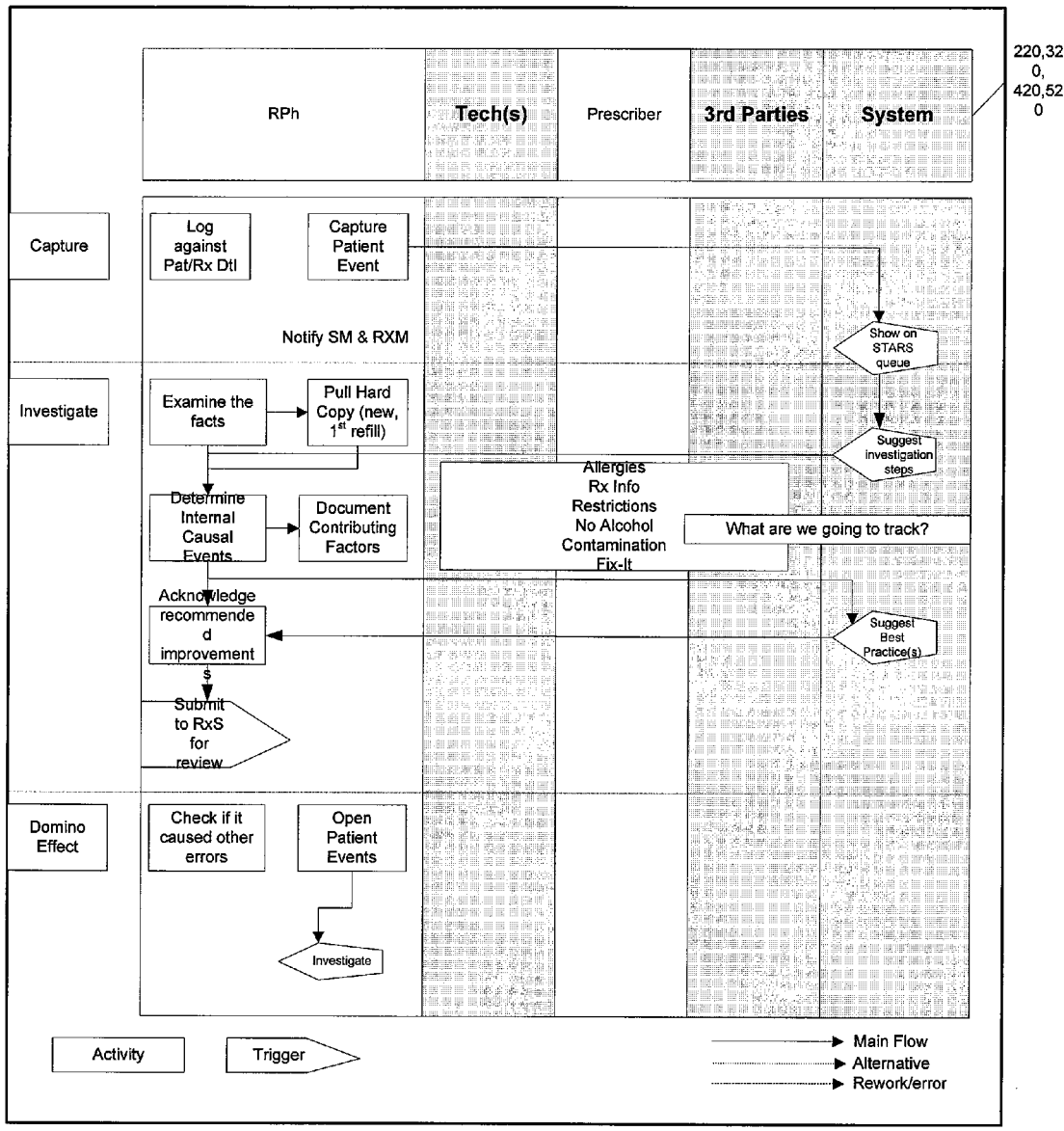
FIG. 22 is a capture and investigate functional flow diagram of the involvement of the personnel with one embodiment of the system of FIG. 1.

Referring to FIG. 22, a capture and investigate functional flow diagram generally shows the capture and investigate activities and triggers and the relationship to one another, by an actor using the system 100. The system 100 and pharmacy error event software 220, 320, 420, 520 implement this functionality as explained above, and as understood by reference to the other portions of this specification.

Figure 23:
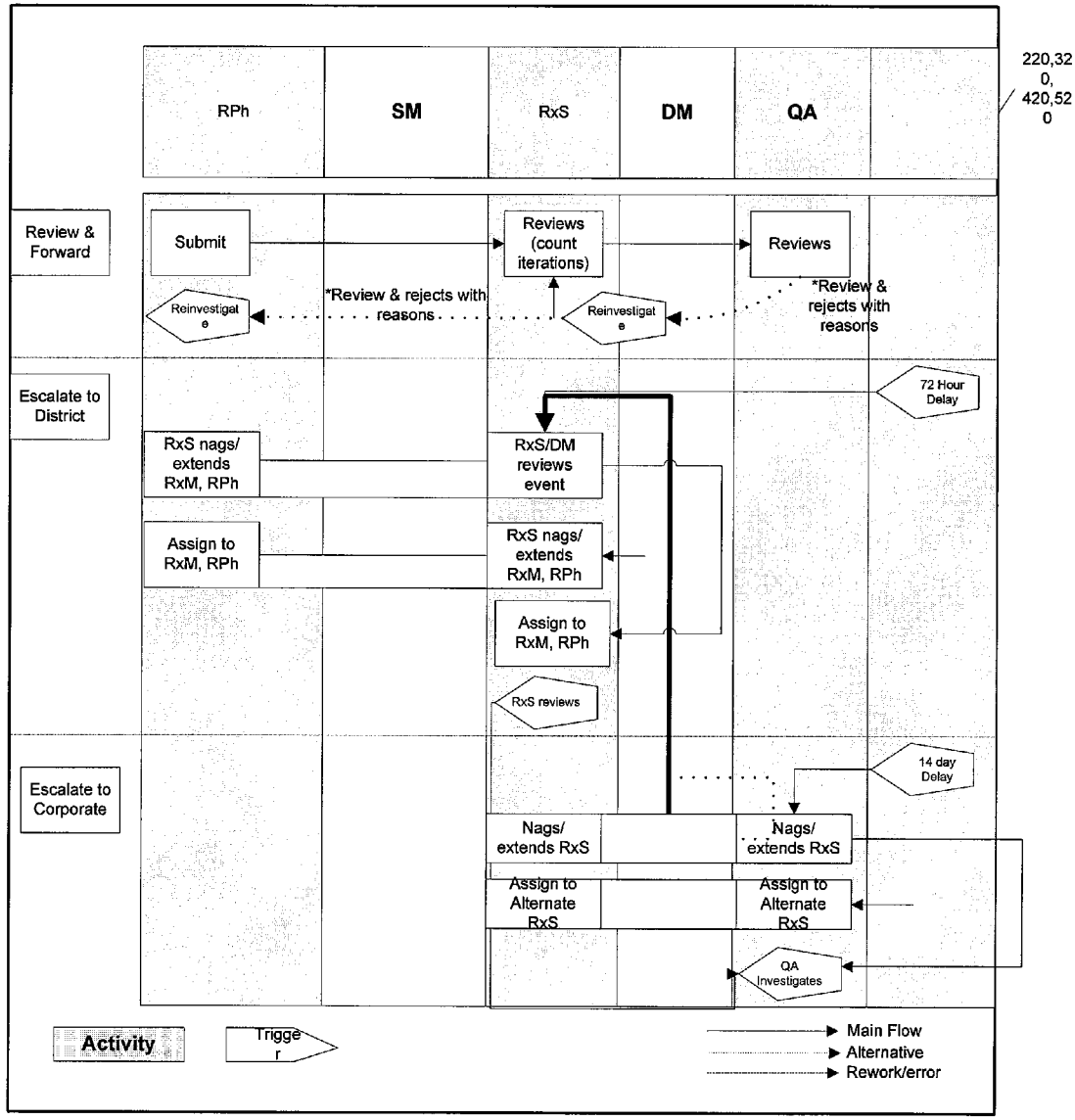
FIG. 23 is an escalation and review investigate functional flow diagram of the involvement of the personnel with one embodiment of the system of FIG. 1; and, FIG. 24 is an assure flow functional flow diagram of the involvement of the personnel with one embodiment of the system of FIG. 1.

Referring to FIG. 23, a escalation review functional flow diagram generally shows the escalation activities and triggers and the relationship to one another, by an actor using the system 100. The system 100 and pharmacy error event software 220, 320, 420, 520 implement this functionality as explained above, and as understood by reference to the other portions of this specification.

Figure 24:
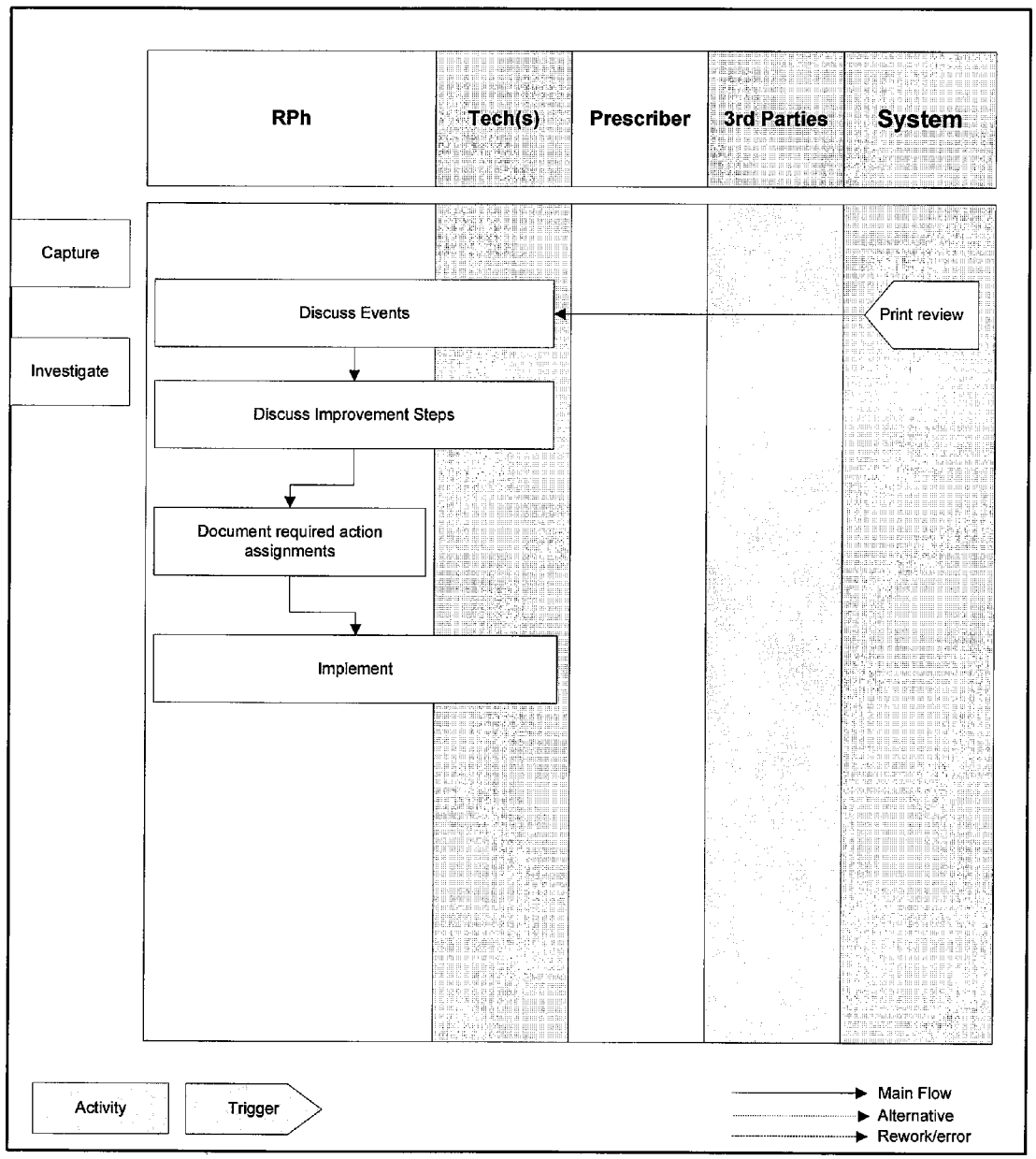

Referring to FIG. 24, a personnel error event review functional flow diagram generally shows some of the error event review activities and triggers and the relationship to one another, by an actor using the system 100, for providing continuous quality improvement. The system 100 and pharmacy error event software 220, 320, 420, 520 implement this functionality as explained above, and as understood by reference to the other portions of this specification.

Any process descriptions or blocks in the figures may be understood as representing modules, segments, or portions of code which include one or more executable instructions for implementing specific logical functions or steps in the process, and alternate implementations are included within the scope of the embodiments of the present invention in which functions may be executed out of order from that shown or discussed, including substantially concurrently or in reverse order, depending on the functionality involved, as would be understood by those having ordinary skill in the art.

It will be understood that the invention may be embodied in other specific forms without departing from the spirit or central characteristics thereof. The present embodiments, therefore, are to be considered in all respects illustrative and not restrictive, and the invention is not to be limited to the details given herein.

What is claimed is:

1. A method of integrated continuous quality improvement in reducing pharmacy error events, comprising the steps of:
receiving pharmacy error event data for each of a first plurality of pharmacy error events through one or more first input devices at a first pharmacy;
transmitting the error event data for each of the first plurality of pharmacy error events to a pharmacy error event database within an pharmacy error event computer;
analyzing the plurality of error event data as a data set with the pharmacy error event computer, wherein the analysis is performed by a criteria for providing first insight information to supervisory personnel;
transmitting tabulated error event data through a communication device to the supervisory personnel; and,
communicating the first insight information to first pharmacy personnel involved with the at least one of the first plurality of pharmacy error events.

2. The method of claim 1, wherein the supervisory personnel is at least one of the following: a store supervisor at the first pharmacy, a district supervisor for a district including the first pharmacy, and/or a corporate supervisor for a plurality of districts including the first pharmacy, wherein each district includes a plurality of pharmacies.

3. The method of claim 1, wherein the step of communicating the first insight information to the first pharmacy personnel comprises sending the first insight information to the first pharmacy personnel through a communications device.

4. The method of claim 1 further comprising the steps of:
receiving error event data for each of a second plurality of pharmacy error events through one or more second input devices at a second pharmacy;
transmitting the error event data for each of the second plurality of pharmacy error events to the pharmacy error event database within the error event computer;
tabulating the error event data with the pharmacy error event computer using pharmacy error event data for each of the first and second plurality of pharmacy error events, wherein the tabulation is performed by a criteria for providing insight information to supervisory personnel, transmitting the tabulated error event data through the communication device to the supervisory personnel in response to the tabulating step; and,
communicating the first insight information to second supervisory personnel of the pharmacy personnel involved with the at least one of the plurality of pharmacy error events.

5. The method of claim 1, wherein the pharmacy error event computer comprises a memory comprising the pharmacy error event database and a pharmacy error event tracking module, wherein the pharmacy error event tracking module is configured to provide at least one functional interface.

6. The method of claim 5 wherein the functional interface is a store interface to manage external events.

7. The method of claim 6, wherein the store interface comprises a display of all external events for a predetermined period of time for a particular pharmacy, wherein the external events are sorted by priority of action, and wherein the external events requiring immediate action are highlighted.

8. The method of claim 7 wherein the functional interface is an employee interface for reviewing respective external events each employee is associated with.

9. The method of claim 8, wherein the employee interface comprises a display of all external events for a predetermined period of time, wherein the external events are sorted by whether the external events have been reviewed and by date of entry of such external event.

10. The method of claim 7 wherein the functional interface is a peer review interface for tracking an improvement focus and for tracking reviewing of posted minutes.

11. The method of claim 10, wherein the peer review interface requires that pharmacy staff sign-off that the improvement focus and/or the posted minutes were reviewed by the pharmacy staff.

12. The method of claim 7 wherein the functional interface is a district review interface for reviewing external events at a district level.

13. The method of claim 12, wherein the district review interface comprises a display of all external events for a predetermined period of time for the pharmacies which a district supervisor is responsible for, wherein each external event displayed is hyperlinked to a detailed event interface for such external event.

14. The method of claim 7 wherein the functional interface is a quality assurance interface for reviewing external events at a corporate level.

15. The method of claim 14, wherein the quality assurance interface are configured to allow a respective district supervisor or corporate/quality assurance supervisor to review, forward, and provide input to evaluate an investigation, findings, and follow-up actions related to each external event, and to reject each external event.

16. The method of claim 7 wherein the functional interface is an external event review interface for reviewing external events in a read-only manner.

\* \* \* \* \*